(12) United States Patent
Demmy

(10) Patent No.: US 10,737,072 B2
(45) Date of Patent: Aug. 11, 2020

(54) CONTROL CATHETERS AND METHODS FOR PULMONARY SUFFUSION AND RELATED THERAPIES

(71) Applicant: SUFFUSION TECHNOLOGIES LLC, Williamsville, NY (US)

(72) Inventor: Todd L. Demmy, East Amherst, NY (US)

(73) Assignee: SUFFUSION TECHNOLOGIES LLC, Williamsville, NY (US)

( * ) Notice: Subject to any disclaimer, the term of this patent is extended or adjusted under 35 U.S.C. 154(b) by 627 days.

(21) Appl. No.: 13/901,542

(22) Filed: May 23, 2013

(65) Prior Publication Data

US 2013/0317535 A1    Nov. 28, 2013

Related U.S. Application Data

(60) Provisional application No. 61/650,516, filed on May 23, 2012.

(51) Int. Cl.
| | |
|---|---|
| *A61M 25/10* | (2013.01) |
| *A61M 25/04* | (2006.01) |
| *A61M 25/01* | (2006.01) |

(52) U.S. Cl.
CPC ......... *A61M 25/1011* (2013.01); *A61M 25/04* (2013.01); *A61M 2025/018* (2013.01); *A61M 2025/1052* (2013.01)

(58) Field of Classification Search
CPC .... A61M 2025/018; A61M 2025/1052; A61M 25/1011
See application file for complete search history.

(56) References Cited

U.S. PATENT DOCUMENTS

| | | | | |
|---|---|---|---|---|
| 4,224,929 A | * | 9/1980 | Furihata | A61B 1/00082 600/107 |
| 4,573,966 A | * | 3/1986 | Weikl | A61M 25/1011 604/101.05 |
| 5,152,277 A | * | 10/1992 | Honda | A61B 1/00082 600/106 |

(Continued)

FOREIGN PATENT DOCUMENTS

| | | |
|---|---|---|
| CN | 1651107 | 8/2005 |
| WO | 2011068946 | 6/2011 |

OTHER PUBLICATIONS

US 7,316,661 B2, 01/2008, Zadno-Azizi et al. (withdrawn)

*Primary Examiner* — Alexander J Orkin
(74) *Attorney, Agent, or Firm* — Meunier Carlin & Curfman LLC

(57) ABSTRACT

The present invention discloses control catheters and methods for pulmonary suffusion and related therapies. The control catheter may comprise a control end, working end having a first balloon, a minor lumen, and a first and second major lumen. One method of the present invention involves introducing the working end of the catheter into a circulator system of the mammal, positioning the catheter into a desired first lobe pulmonary artery, inflating the minor balloon using the corresponding lumen, positioning the major balloon in the main pulmonary artery, and inflating the major balloon using the corresponding lumen. The method may comprise the additional step of infusing a chemical agent through the distal tip after the inflation of the minor balloon and the major balloon.

18 Claims, 22 Drawing Sheets

(56) References Cited

U.S. PATENT DOCUMENTS

| | | | |
|---|---|---|---|
| 5,460,610 A * | 10/1995 | Don Michael | A61M 25/0133 |
| | | | 604/101.03 |
| 5,558,644 A * | 9/1996 | Boyd | A61B 17/29 |
| | | | 604/102.02 |
| 5,584,803 A * | 12/1996 | Stevens | A61B 17/29 |
| | | | 604/101.01 |
| 6,306,097 B1 | 10/2001 | Park et al. | |
| 6,494,905 B1 * | 12/2002 | Zedler | A61F 2/958 |
| | | | 623/1.11 |
| 6,575,932 B1 * | 6/2003 | O'Brien | A61M 25/007 |
| | | | 604/101.01 |
| 6,595,953 B1 * | 7/2003 | Coppi | A61B 17/12045 |
| | | | 604/93.01 |
| 6,682,499 B2 | 1/2004 | Lenker | |
| 6,685,648 B2 | 2/2004 | Flaherty et al. | |
| 7,179,251 B2 | 2/2007 | Palasis | |
| 7,229,464 B2 | 6/2007 | Hanson et al. | |
| 7,232,427 B2 | 6/2007 | Propp | |
| 7,803,171 B1 | 9/2010 | Uflacker | |
| 8,118,803 B1 | 2/2012 | Chow | |
| 8,162,879 B2 | 4/2012 | Hattangadi et al. | |
| 2003/0204138 A1 * | 10/2003 | Choi | A61M 25/1011 |
| | | | 600/434 |
| 2004/0068226 A1 * | 4/2004 | Brannon | A61M 25/1011 |
| | | | 604/101.01 |
| 2008/0082046 A1 | 4/2008 | Kato et al. | |
| 2008/0312636 A1 | 12/2008 | Miller et al. | |
| 2009/0124999 A1 * | 5/2009 | Horton | A61M 25/0068 |
| | | | 604/514 |
| 2010/0222637 A1 * | 9/2010 | Kassab | A61B 5/02152 |
| | | | 600/17 |
| 2012/0259215 A1 * | 10/2012 | Gerrans | A61M 25/1011 |
| | | | 600/435 |

* cited by examiner

CONTROL CATHETERS AND METHODS FOR PULMONARY SUFFUSION AND RELATED THERAPIES

CROSS-REFERENCE TO RELATED APPLICATIONS

This application claims priority to U.S. Provisional Application No. 61/650,516 filed on May 23, 2012, now pending, the disclosure of which is incorporated herein by reference.

FIELD OF THE INVENTION

The invention relates generally to control catheters and methods for therapeutic interventions using control catheters, for example, selective pulmonary suffusion.

BACKGROUND OF THE INVENTION

There are millions of patients who have life-threating lung conditions for which there are potential pharmacologic therapies. Some examples of these diseases are lung cancer (primary), secondary lung cancer (metastases to the lung), pulmonary hypertension, Adult Respiratory Distress Syndrome ("ARDS"), asthma, lung organ rejection, and others. Unfortunately, such pharmacologic remedies are tolerated poorly by the ill patients who have these conditions because the drugs are toxic, potent, and delivered to the entire body rather than the lung organ where most of the pathology resides. There is an ongoing need for a minimally invasive system to control lung circulation for targeting drug delivery.

The promise of selectively delivered chemotherapy has long been recognized. This approach has been used most notably in isolated limb perfusion for melanoma and sarcoma as well as hepatic perfusion for unresectable liver tumors and metastases from colorectal cancer. In adopting this technology for the effective treatment of pulmonary tumors, similar techniques have been explored using isolated lung perfusion. These techniques require thoracotomy incisions for cannulation of delicate pulmonary vessels or risked toxic chemotherapy leakage into the systemic circulation.

In particular, while regional chemotherapy has been established as an effective means to target therapeutic agents, complexities in the lung circulation and the need for large incisions have limited its use in the chest. While catheters have been designed for placement through the heart and into the pulmonary artery (such as the Swan-Ganz catheter, which has been used for over 40 years), the balloons on these devices are too small to completely occlude the main pulmonary artery. Larger versions of such catheters exist that can occlude the main branch pulmonary artery. Unfortunately, such larger versions do not both reliably occlude the main pulmonary artery and provide predictable drainage and infusion access to all the branch vessels. This is because the branch vessels are short and variable in their conformations (see, for example, FIGS. 21A and 21B).

Attempts to develop systems for selective control of variable branches for windpipes have been made, such as by the use of a double lumen endotracheal tube design, but such devices have not been applied for vascular control, nor have they been suggested for administration of an agent for disease prophylaxis and/or therapy. Current balloon catheters tend to be unstable when positioned in the right or left main pulmonary artery because these arteries continue for very short distances before branching. Thus, they either dislodge from their intended position. If positioned deeper in the vessel, they migrate past important branches and miss large portions of the targeted organ. Accordingly, the present invention provides an improved catheter and systems and methods for use in prophylaxis and/or therapy of disease.

BRIEF SUMMARY OF THE INVENTION

The present invention solves these and other problems. The present invention is different from earlier methodologies and involves permeation of the chemotherapeutic agent throughout the lung without use of perfusion apparatus (described herein as lung suffusion). The present invention also advantageously allows for the positioning of one or more anchor wires to stabilize the catheter in a branched vessel.

In one embodiment, the invention can be described as a catheter comprising a control end, a working end, a minor lumen, and a first and second major lumen. The catheter may be configured for use in a pulmonary artery of an individual. For example, the length of the catheter and space between components may be selected such that the components can be easily positioned in the pulmonary artery. In one embodiment, the catheter has a size of 8-11 F.

The working end has a first balloon. The first balloon may have an inflated diameter of 20-30 mm. In one embodiment, the working end further comprises a second balloon in fluid communication with a second minor lumen. The second balloon may be configured to be selectively inflated. The second balloon may be distally located with respect to the first balloon.

The minor lumen extends from the control end to the first balloon. The minor lumen is in communication with the first balloon such that the first balloon can be selectively inflated by way of the minor lumen. The minor lumen may have a size of 1-2 F.

The first major lumen extends from the control end to a location at the working end which is distal with respect to the first balloon. For example, the first major lumen may extend to a location at the working end which is 25-100 mm distal with respect to the first balloon. In another embodiment, the first major lumen may extend to a location between the first balloon and the second balloon (if present). In one embodiment, the first major lumen may be configured to accept another catheter. For example, the first major lumen may be configured to accept a flow-directed pulmonary artery catheter. In another embodiment, the first major lumen may be configured to receive an anchoring wire.

The second major lumen extends from the control end to a location at the working end which is distal with respect to the first balloon. The first major lumen and/or second major lumen have a size of 4-8 F. In embodiments with a second balloon, the second major lumen may extend to a location distal to the second balloon. In embodiments where the first major lumen may be configured to receive an anchoring wire, the second major lumen may terminate at a port configured to allow infusion or drainage. The port may be located proximal with respect to the first balloon or distal with respect to the second balloon.

In another embodiment, the catheter further comprises a deflector. The deflector may be configured to deflect an anchoring wire and located at the distal end of the first major lumen. The anchoring wire is inserted into the first major lumen through the deflector. After being deflected, the anchoring wire travels into a branch vessel of a main vessel such that the catheter remains substantially stationary. The deflector may be a ramp or a bead.

In another embodiment, the catheter further comprises a venting hole. The venting hole is in fluid communication with the first major lumen. The venting hole may be distally located with respect to the first balloon.

The invention may also be described as a catheter comprising a control end, a first lumen, a second lumen, a third lumen, and a working end. The control end may be configured for manipulation by an operator. In one embodiment, the first lumen and second lumen have a size of 1-2 F. In another embodiment, the third lumen is configured such that a stabilization wire may be introduced by an operator into the third lumen. For example, the third lumen may have a size of 5 F. The primary lumen may be in communication with a port at the control end of the catheter for introduction or removal of a fluid.

The working end comprises a major balloon, minor balloon, accessory orifice, and a distal tip. The major balloon is in fluid communication with the first lumen and is configured to be selectively inflated. The major balloon may be configured to occlude blood flow in a main pulmonary artery of a patient when inflated.

The minor balloon is distally located along the catheter with respect to the major balloon. The minor balloon is in fluid communication with the second lumen and configured to be selectively inflated. The minor balloon may be configured to occlude blood flow in a branch pulmonary artery of a patient when inflated.

The accessory orifice is located between the major balloon and the minor balloon. The accessory orifice is in communication with the third lumen. The accessory orifice may be oriented at 90 degrees with respect to a reference axis of the catheter. In one embodiment, the third lumen has a deflection ramp configured to assist the movement of an accessory through the accessory orifice. The angle of the deflection ramp may be configured to facilitate the positioning of one or more accessories into an upper lobe branch vessel of a lung.

The distal tip is distally located along the catheter with respect to the minor balloon. The distal tip has an orifice in communication with a primary lumen. The primary lumen may be configured to drain fluid from a location at the distal tip.

The invention may also be described as a method for selectively controlling pulmonary circulation in an individual using a catheter. In one embodiment of the method, the catheter has a control end, a plurality of lumens and, a working end. The working end has a major balloon and a minor balloon, an accessory orifice located between the major balloon and the minor balloon, and a distal tip distally located along the catheter with respect to the minor balloon.

The method may comprise the steps of introducing the working end of the catheter into a circulator system of the mammal, positioning the catheter into a desired first lobe pulmonary artery, inflating the minor balloon using the corresponding lumen, positioning the major balloon in the main pulmonary artery, and inflating the major balloon using the corresponding lumen.

In one embodiment, the minor balloon may be inflated until there is a reduction in pulsatile distal lumen arterial waveform. In another embodiment, the method may further comprise the step of delivering a dye through the accessory orifice to confirm placement and proper obstruction of the pulmonary arteries.

In another embodiment, the method may further comprise the steps of deflating the minor balloon and major balloon, inserting a guide wire through the accessory orifice into a second lobe artery, repositioning the minor balloon and major balloon, and inflating the minor balloon and major balloon.

In one embodiment, the method may further comprise the step of infusing a chemical agent through the distal tip after the inflation of the minor balloon and the major balloon.

The invention may also be described as a method for anchoring a catheter in an individual. The catheter may have a working end and a first lumen. The method comprises the steps of introducing the working end of the catheter into a circulator system of the mammal, positioning the catheter into a desired artery having a first branch and a second branch, introducing an anchor wire into the first branch by way of the first lumen, and deploying the first anchor in the first branch using the corresponding lumen to anchor the catheter in the individual. In one embodiment, the method may further comprise the step of deploying a second anchor wire in the second branch by way of a second lumen.

DESCRIPTION OF THE DRAWINGS

For a fuller understanding of the nature and objects of the invention, reference should be made to the following detailed description taken in conjunction with the accompanying drawings, in which.

DETAILED DESCRIPTION OF THE INVENTION

The present invention provides systems, an apparatus, methods, and compositions for use in therapeutic interventions. The interventions relate generally to use of a catheter provided by the invention to deliver one or more therapeutic agents to an individual in need of prophylaxis and/or therapy of one or more conditions.

It will be recognized by those skilled in the art that the present invention provides a solution to a longstanding problem. The catheter and system of embodiments of the present invention facilitate delivery of an effective amount of an agent to an individual in need thereof.

In general, the invention provides a catheter system which facilitates reliable control of the main arteries going to the right or left lung of an individual for the purpose of affecting the function of the circulatory system of the individual, such as for vascular occlusion, vascular drainage, and/or introduction of various chemical agents into the lung (or other or organ). In one embodiment, the system is based in part on a set of in-line occlusion balloons and multiple catheter channels configured for the unique arterial anatomy of the lung, specific exemplary embodiments of which are further described below. Some embodiments of the invention are designed to enhance various drug or immune therapies for diseases that are too toxic to be safely treated by delivering the drug to the entire body using conventional techniques.

Catheter

Figure 1:
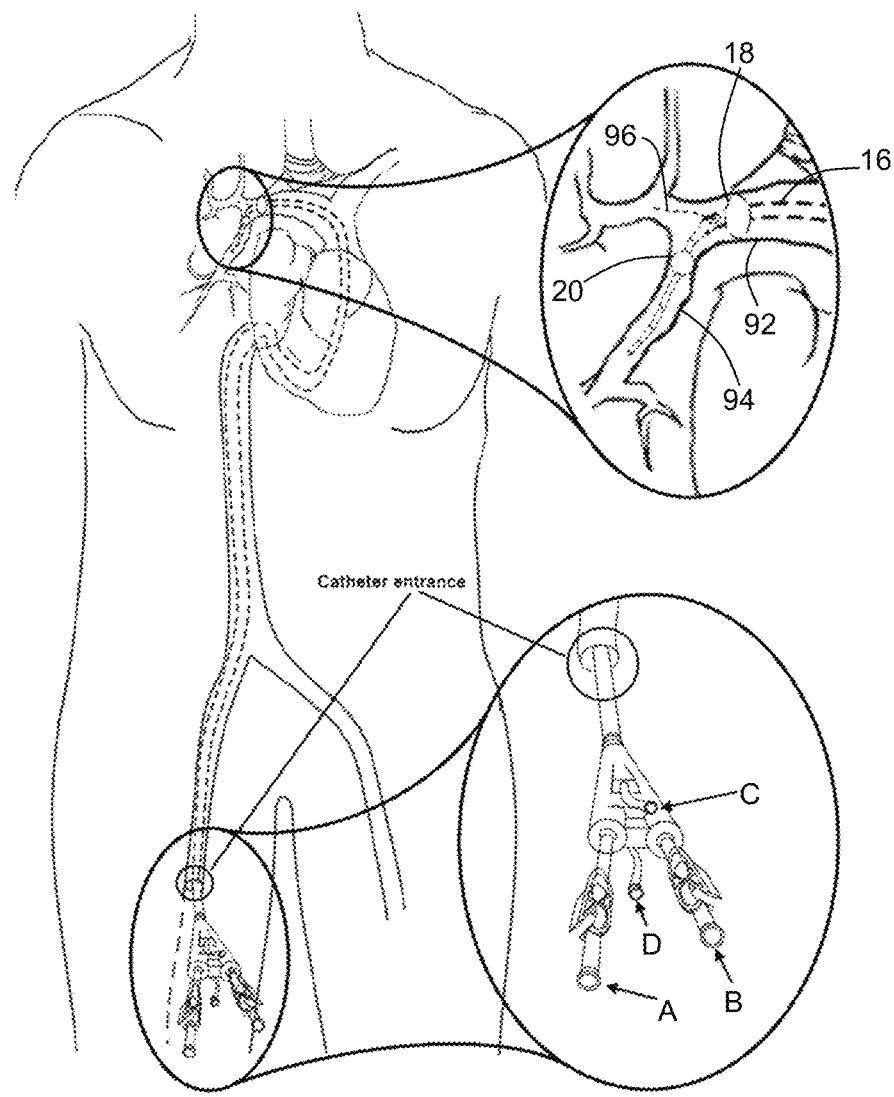
FIG. 1 is an anatomical diagram showing a catheter according to an embodiment of the present invention in place and having an inset diagram depicting an exemplary in situ placement of an operable end of the catheter and an inset diagram showing a distal end of the catheter.
Figure 3:
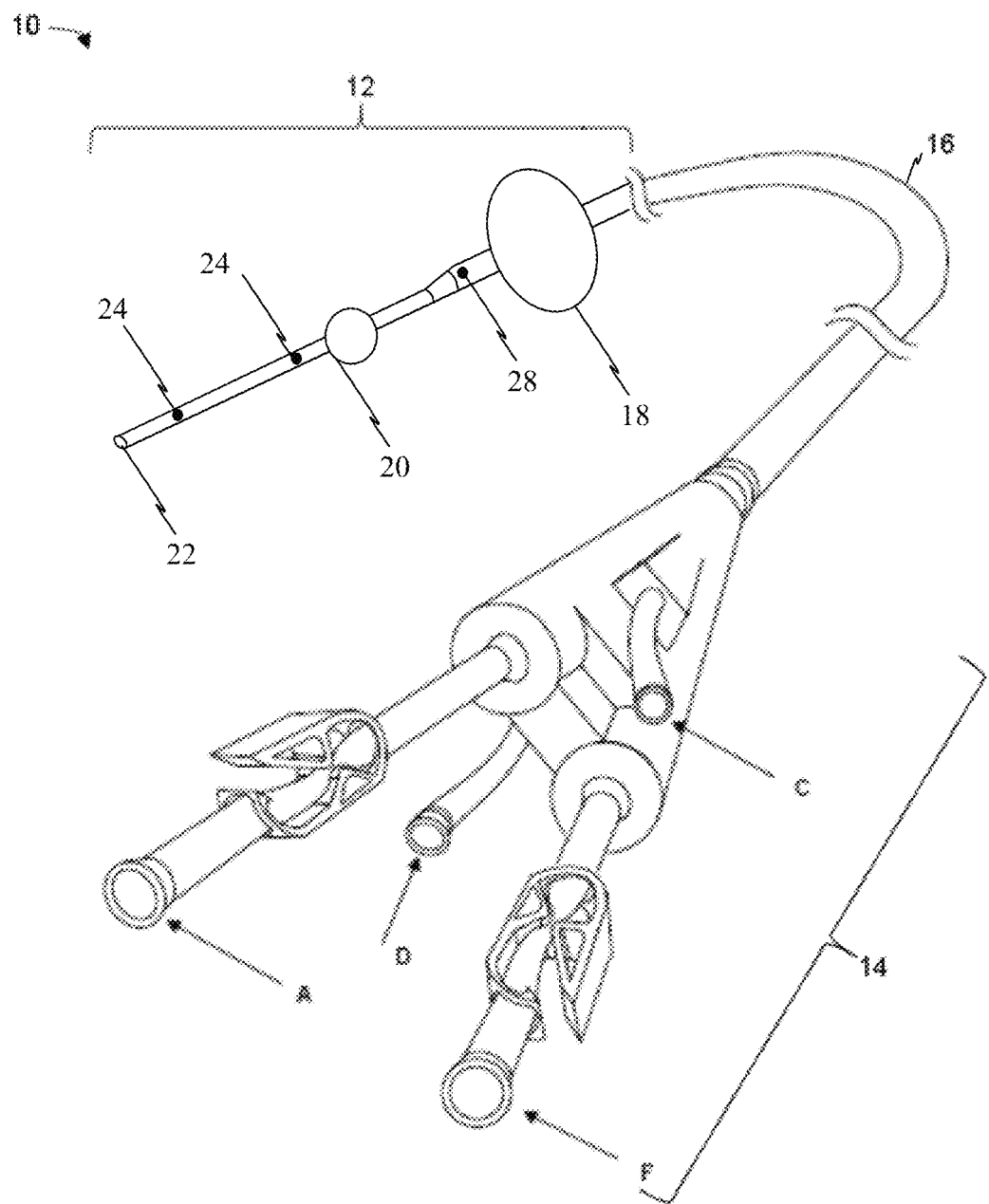
FIG. 3 is a diagram of portions of a catheter according to another embodiment of the present invention.
Figure 4:
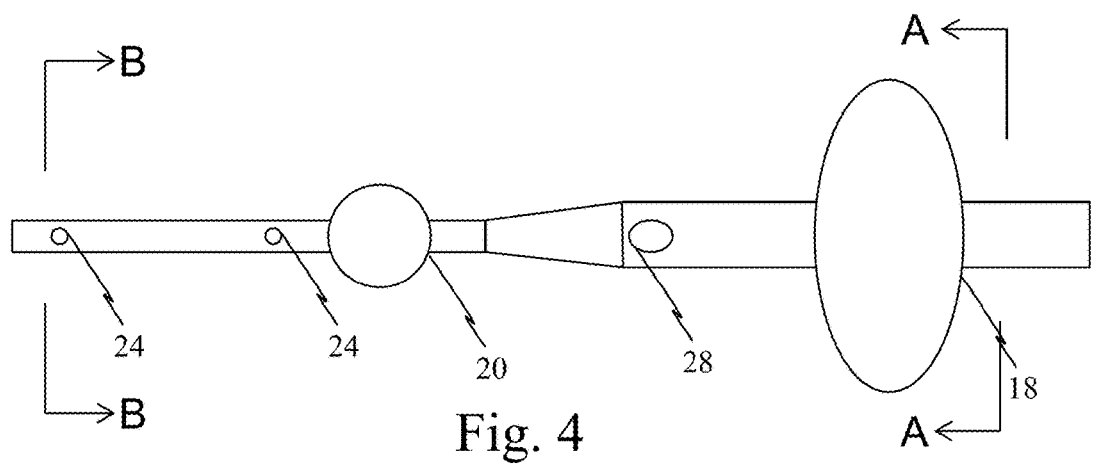
FIG. 4 is a top view of a distal end of a catheter according to another embodiment of the present invention.

FIG. 1 depicts a catheter 10 according to an embodiment of the present invention which allows selective control of the pulmonary circulation. It should be noted that embodiments of the present invention may be used for selective control of circulation in organs other than the lung, and that such embodiments are within the scope of the present invention. Catheter 10 comprises a line 16 having one or more lumens as further described below. FIG. 3 shows an embodiment of the present invention having a line 16 which has a working end 12, configured for insertion into an individual, and a control end 14, configured for manipulation by an operator, for example, a surgeon. In some embodiments, the material of the catheter has a durometer of 55-70 shore D.

Figure 2A:
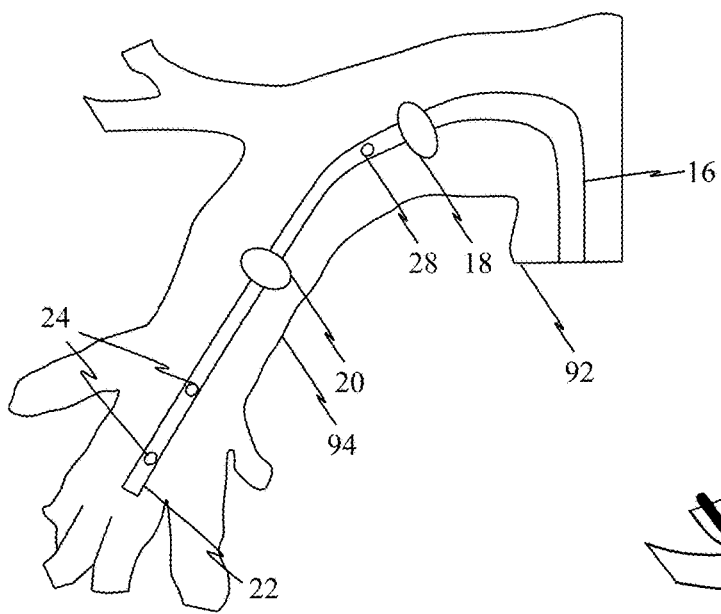
FIG. 2A depicts a catheter according to another embodiment of the present invention in situ with balloons deflated.
Figure 13:
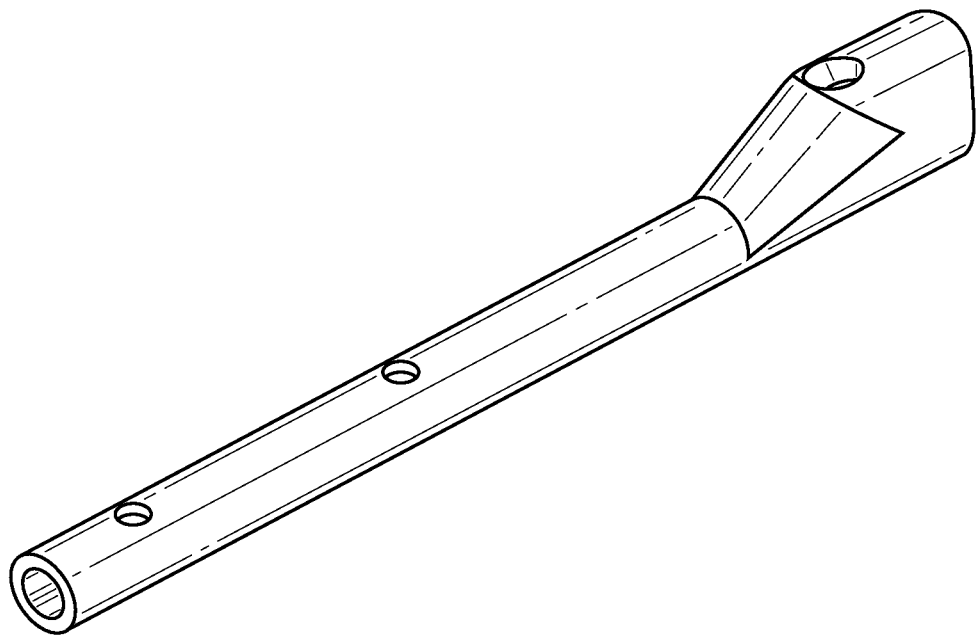
FIG. 13 is a perspective view of a portion of a catheter according to another embodiment of the present invention.
Figure 14:
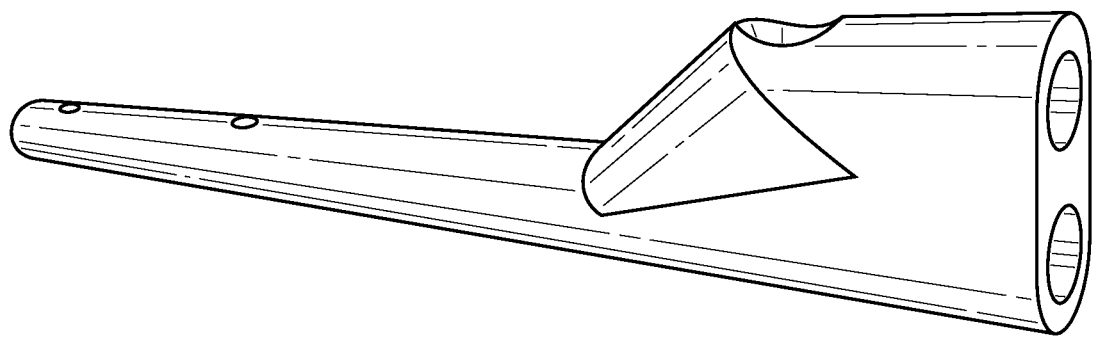
FIG. 14 is a perspective view of the catheter portion of FIG. 13.

The working end 12 of the line 16 has a major balloon 18 and a minor balloon 20. The minor balloon 20 is distally located along the line 16 with respect to the major balloon 18. Each balloon 18,20 is in communication with a respective lumen of the line 16. In this way, each balloon 18,20 may be selectively inflated and deflated by the operator. The lumens may be of any appropriate size, such as, for example, 1 F. Other sizes may include 2 F, 3 F, 4 F and any size in between. Major balloon 18 is configured to occlude blood flow in the main artery 92 of a lung when major balloon 18 is inflated (see, e.g., FIGS. 2A, 2B, and 2D). Minor balloon 20 is configured to occlude blood flow in a branch artery 94 of the lung when minor balloon 20 is inflated. FIGS. 13 and 14 depict another embodiment of a working end 12 without major balloon 18 and minor balloon 20 visible.

Line 16 further comprises an accessory orifice 28 located between the major and minor balloons 18, 20. The accessory orifice 28 is in communication with an accessory lumen 30 of the line 16 and configured such that a stabilization wire 96 may be introduced by an operator into the accessory lumen 30 at the control end 14 of the catheter 10 and fed through the line 16 until a portion of the stabilization wire 96 extends through the accessory orifice 28. In other embodiments, the catheter 10 is configured such that a further catheter, guide wire, thermistor, and/or other advantageous accessories may be introduced by way of the accessory lumen 30 and accessory orifice 28. As such, the accessory lumen 30 may be of any size, such as, for example, 5 F. In other embodiments, the accessory lumen 30 may be 1 F, 2 F, 3 F, 4 F, 6 F, 7 F and any size in between.

A distal tip 22 of the line 16 extends beyond the minor balloon 20 and has one or more distal orifices 24. The distal orifice 24 is in communication with a primary lumen 26 of the line 16, such that a distal tip 22 of the catheter 10 is in communication with a port at the control end 14 and accessible by the operator. In this way, actions may be performed to, for example, drain fluid (e.g., blood) from a location at the distal tip by way of the primary lumen 26.

Figure 5:
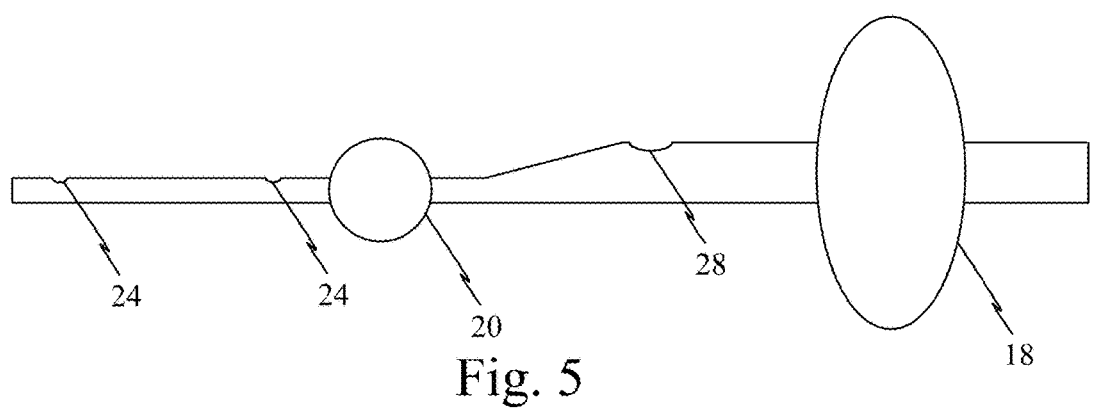
FIG. 5 is a side-elevation view of the distal end of FIG. 4.
Figure 6:
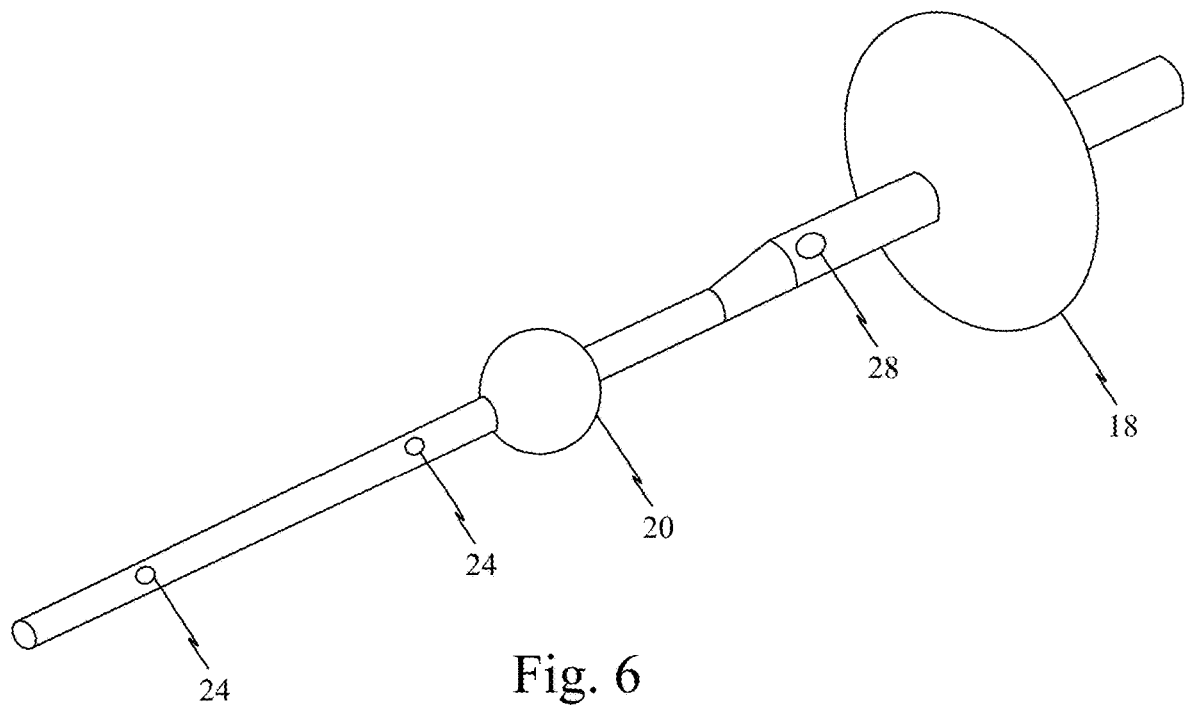
FIG. 6 is a perspective view of the distal end of FIGS. 4 and 5.
Figure 7:
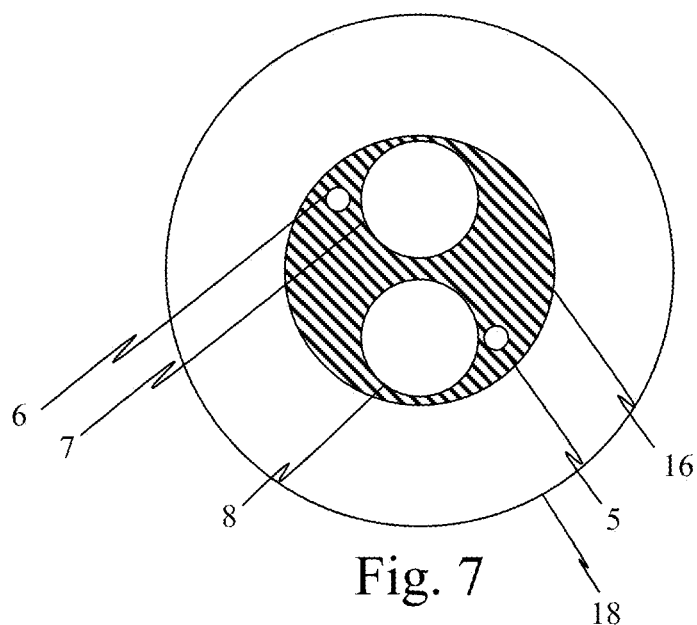
FIG. 7 is a partial cross-sectional view of the distal end of FIGS. 4-6 taken along section A-A of FIG. 4.
Figure 8:
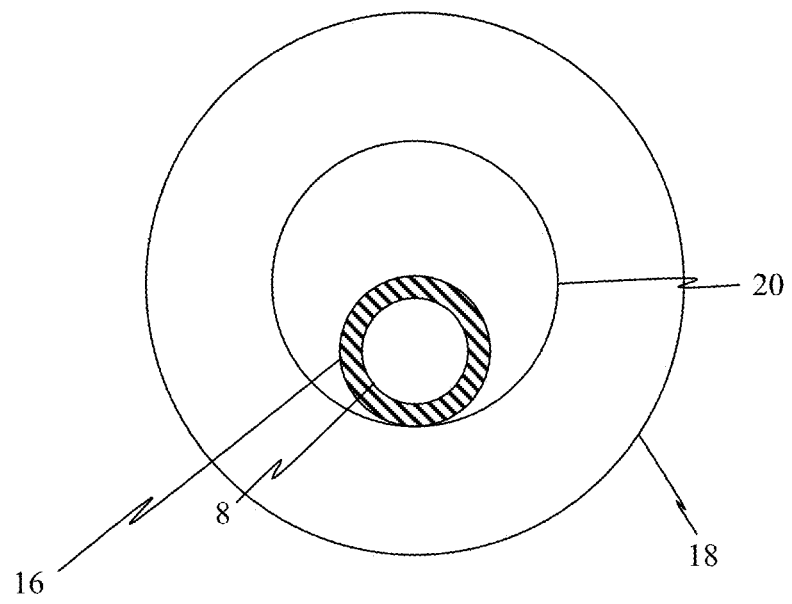
FIG. 8 is a partial cross-sectional view of the distal end of FIGS. 4-6 taken along section B-B of FIG. 4.
Figure 9:
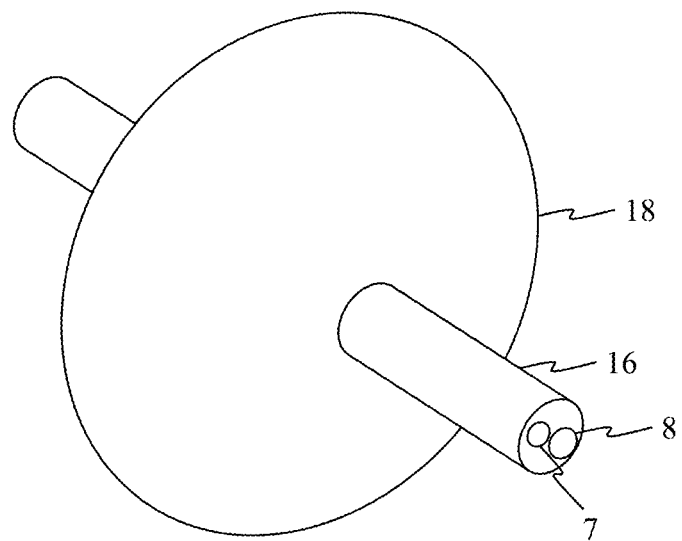
FIG. 9 is a perspective view of the major balloon of the catheter of FIGS. 4-6.
Figure 10:
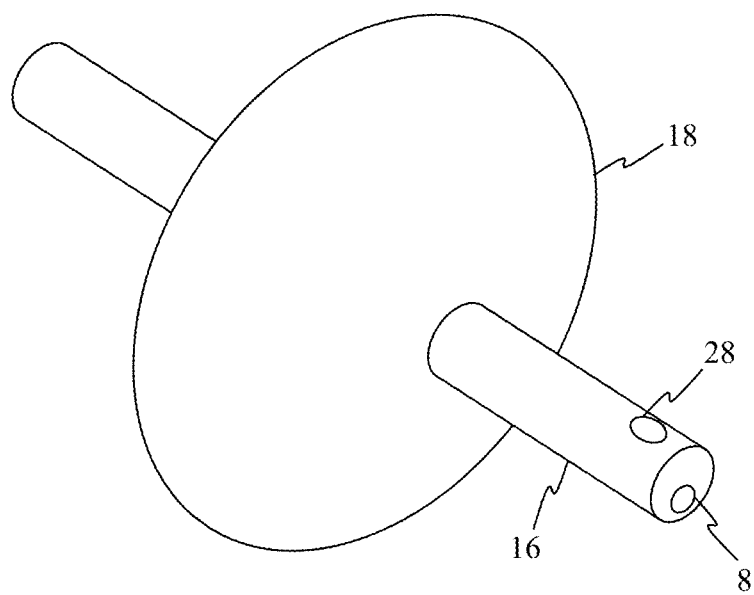
FIG. 10 is a perspective view of the minor balloon of the catheter of FIGS. 4-6.
Figure 11A:
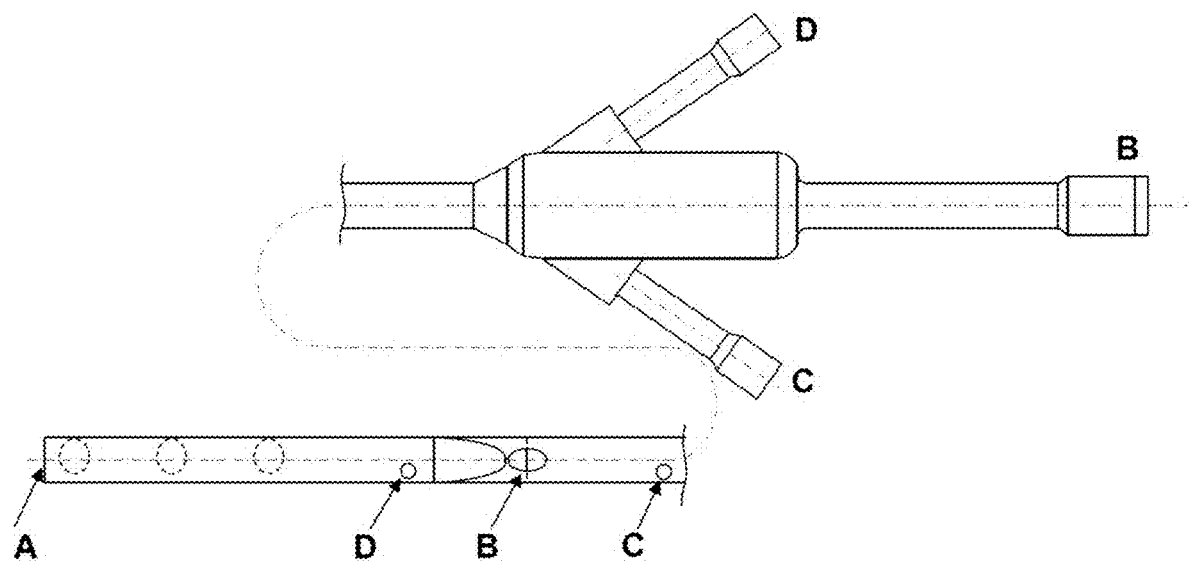
FIG. 11A is a partial top view of a catheter of another embodiment according to the present invention.
Figure 11B:
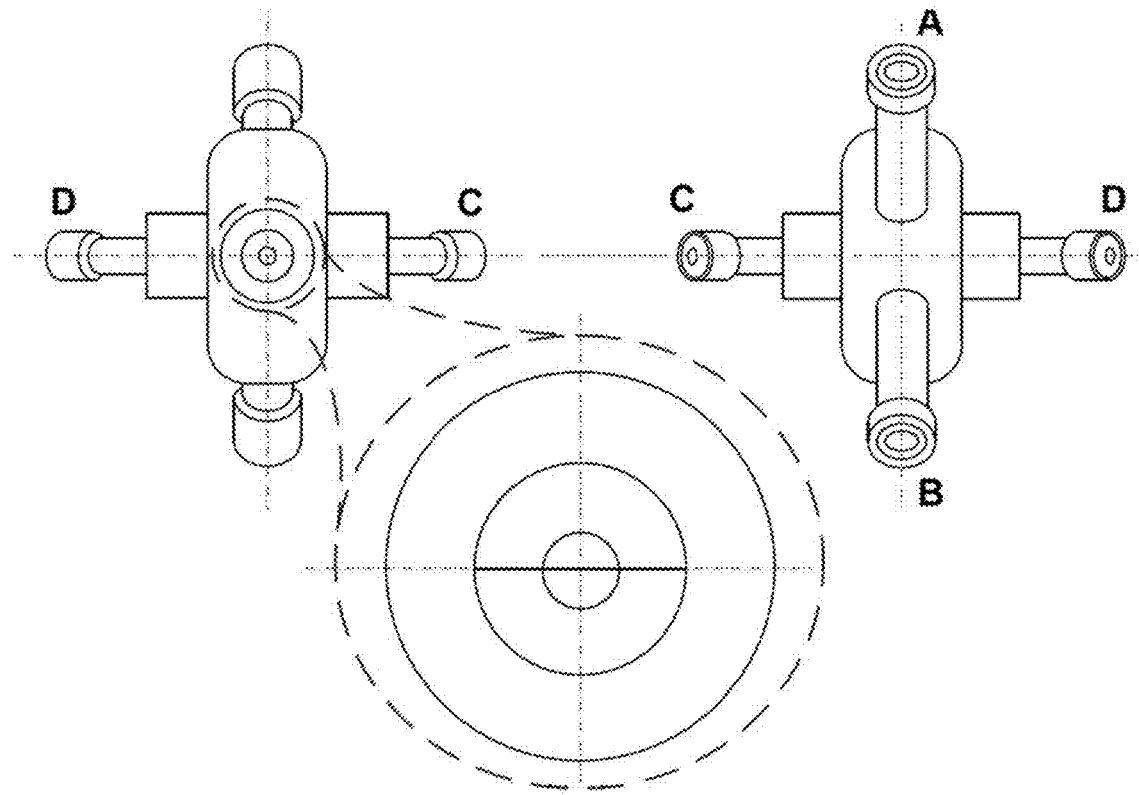
FIG. 11B depicts two end views of the catheter of FIG. 11A and an inset detail view.
Figure 12:
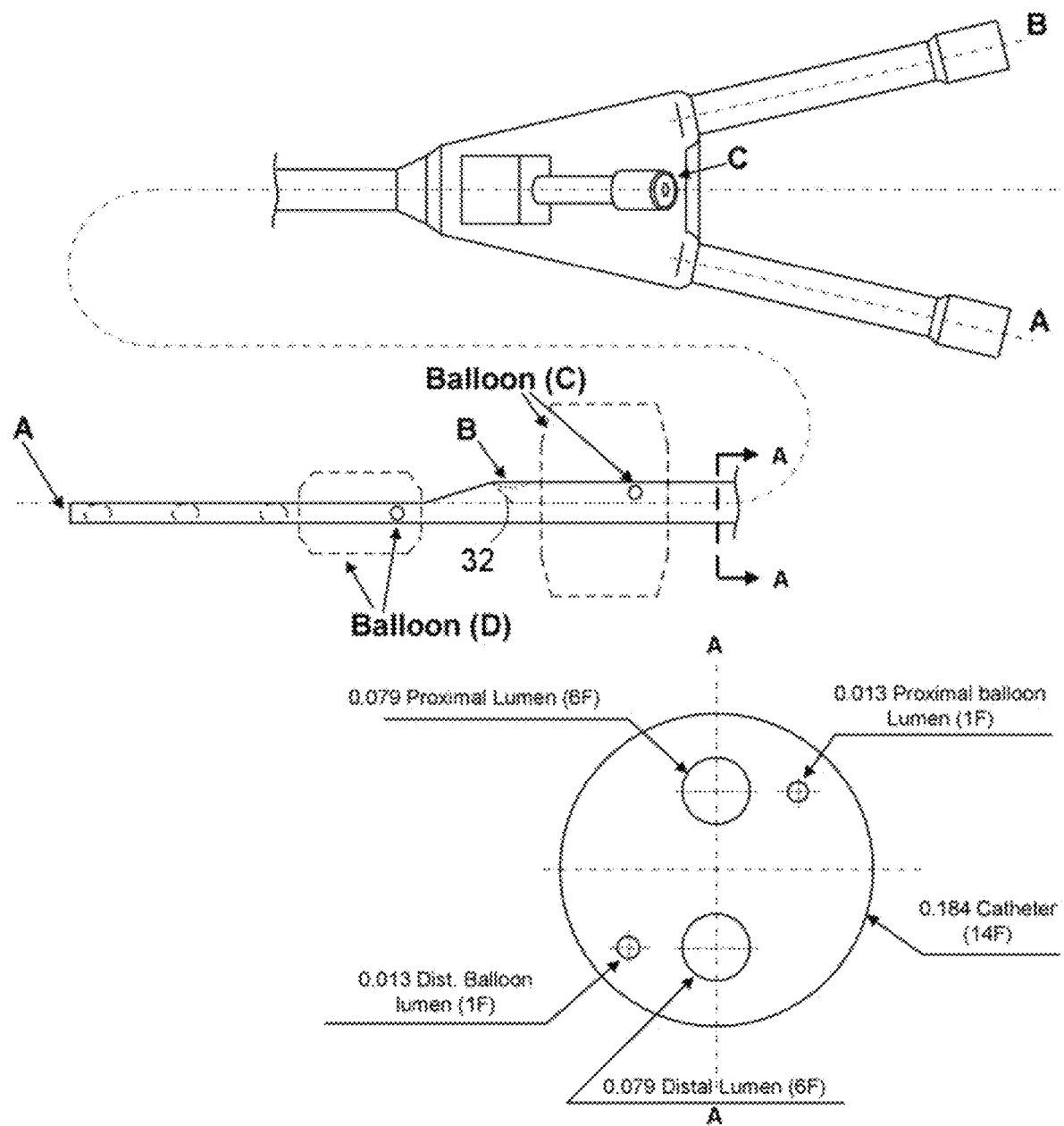
FIG. 12 is a partial side view of the catheter of FIGS. 11A and 11B and having an inset cross-section view taken along A-A of the instant Figure.

A cross-sectional view of the catheter 10 is shown in FIGS. 7 and 8. FIG. 7 is the cross-section at A in FIG. 5 and FIG. 8 is the cross-section at B in FIG. 5. In FIG. 7, minor lumens 5 and 6 are visible. Also visible are first major lumen 7 and second major lumen 8. These lumens will be described in further detail below. FIG. 8 illustrates the distal termination of some of the lumens such that the only lumen visible is second major lumen 8. A perspective view of the catheter 10 is shown in FIGS. 9 and 10. FIGS. 9 and 10 show catheter 10 cut before and after major balloon 18, but from opposite perspectives.

Figure 15:
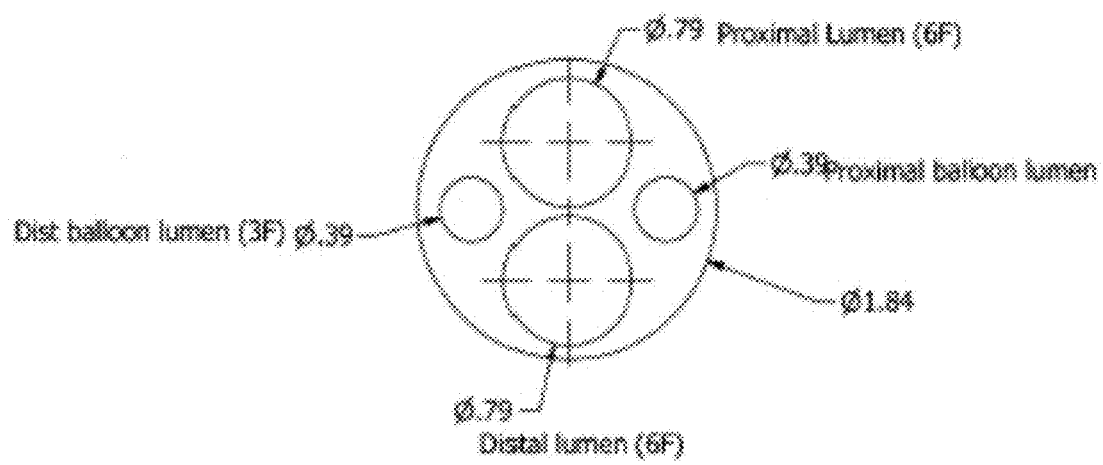
FIG. 15 is a cross-section view of a catheter according to another embodiment of the present invention.
Figure 16A:
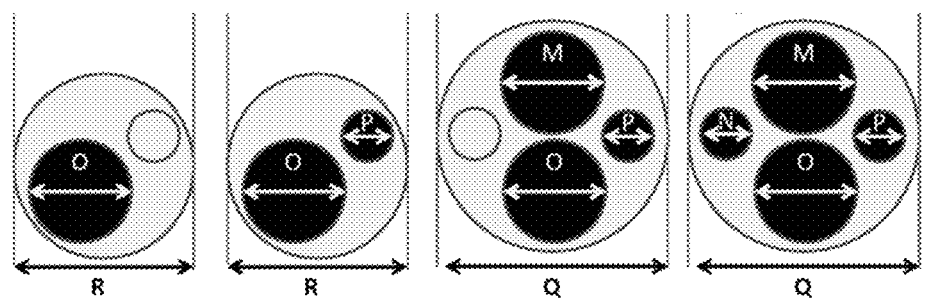
FIG. 16A is a cross-section view of a catheter at various points in the catheter according to another embodiment of the present invention.
Figure 16B:
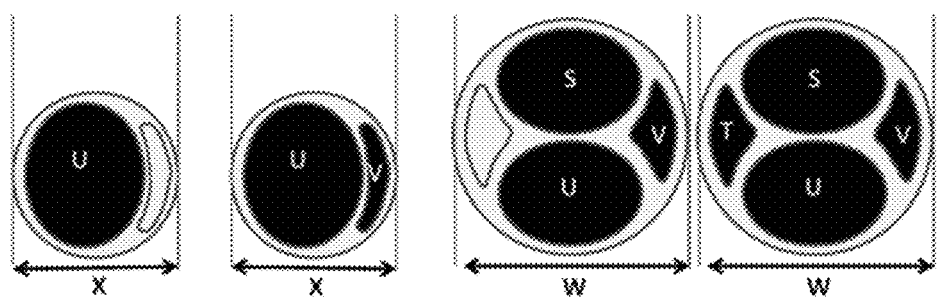
FIG. 16B is a cross-section view of a catheter at various points in the catheter according to another embodiment of the present invention.
Figure 17:
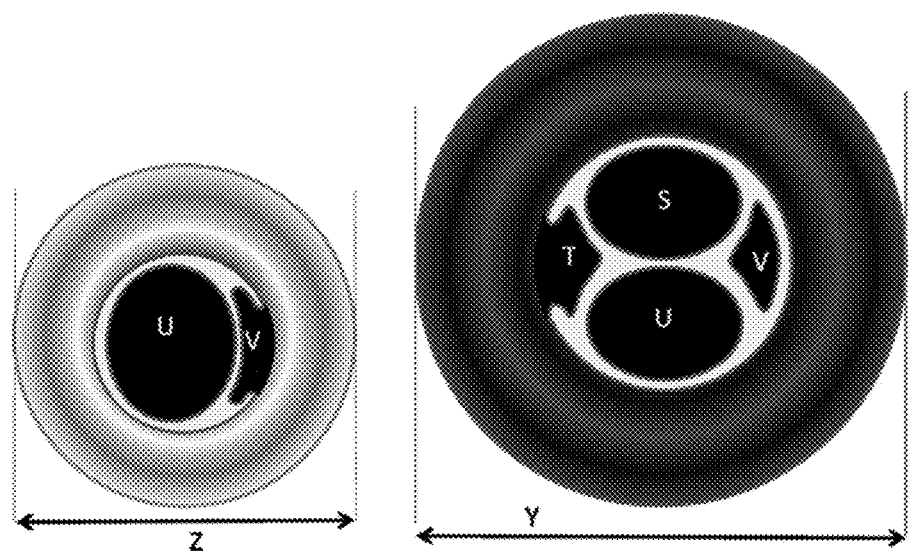
FIG. 17 is a multiple cross-section view of the catheter of FIG. 16B including balloons.
Figure 18:
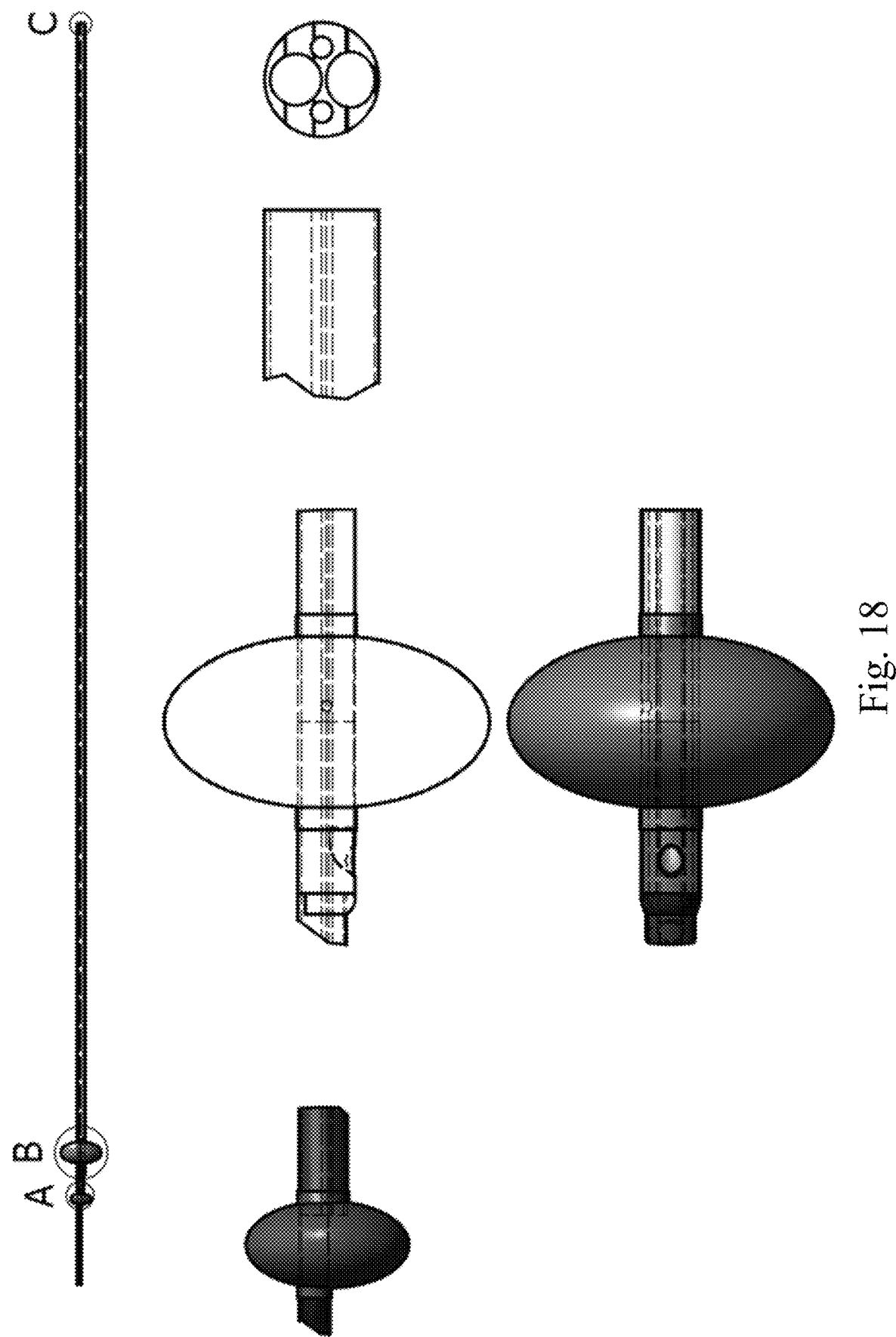
FIG. 18 is an exploded, partial side view of a catheter according to another embodiment of the present invention.
Figure 19:
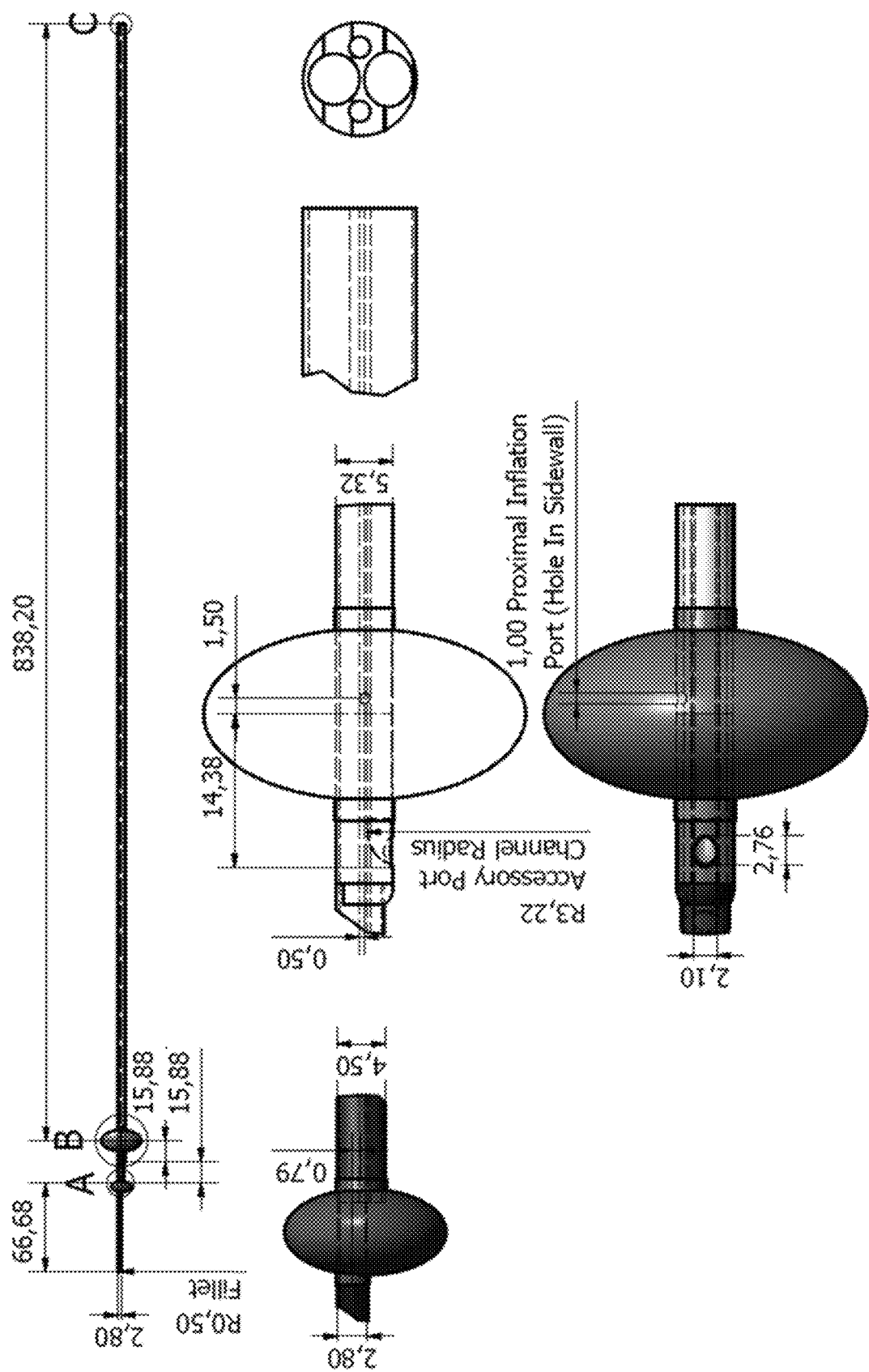
FIG. 19 is an exploded, partial side view with dimensions according to an exemplary embodiment of the present invention.

The lumens of catheter 10 may be organized in various dimensions and shapes. FIG. 15 depicts a cross-sectional view of one embodiment of a catheter 10. FIGS. 16A and 17A depict multiple cross-sectional views at different areas of a catheter according to the present invention. The lumens shown in FIG. 16B are not strictly circular and are configured to maximize the space of each lumen without increasing the overall diameter of the catheter. FIG. 17 illustrates openings in the lumens of FIG. 16B for the selective inflation and deflation of the major and minor balloons.

Figure 25A:
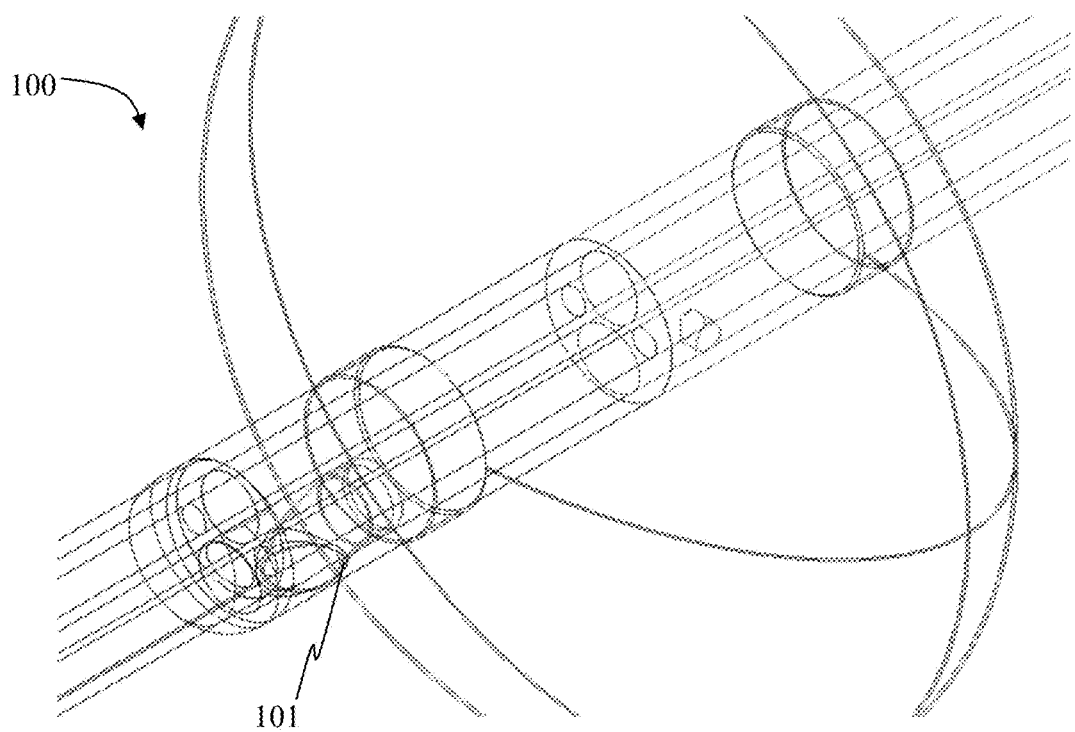
FIG. 25A is magnified perspective view of the first balloon of the catheter of FIG. 22A.
Figure 25B:
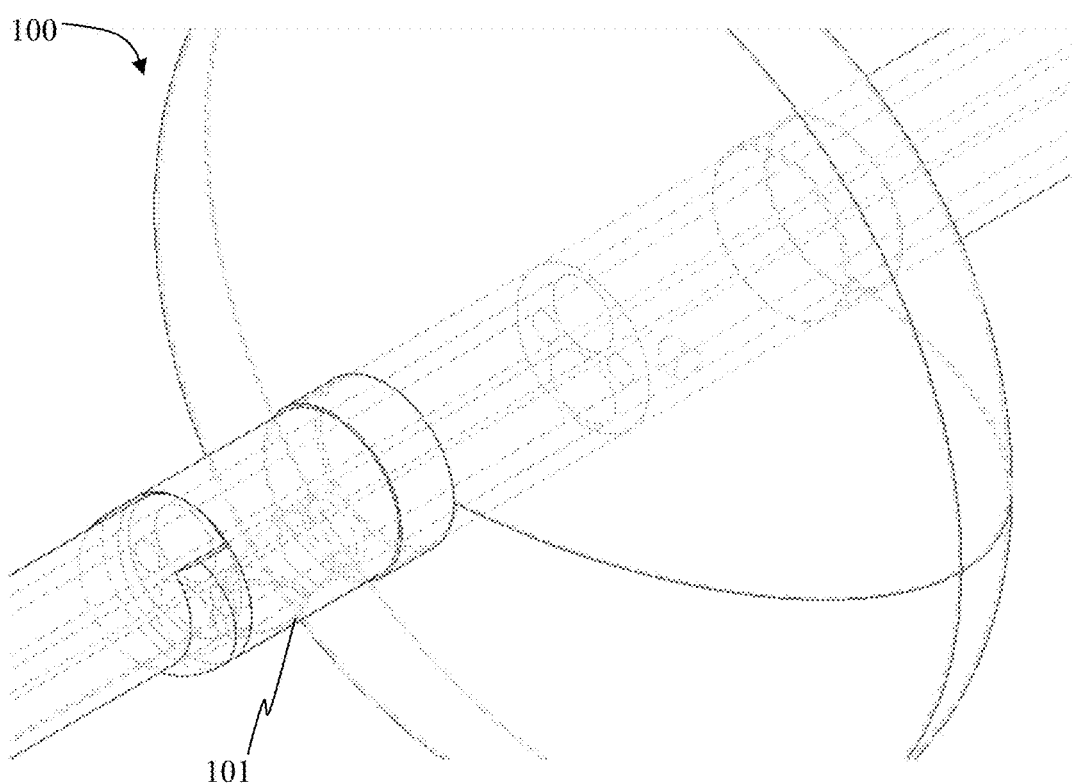
FIG. 25B is magnified perspective view of the first balloon of the catheter of FIG. 22A showing interior lines.

The accessory orifice 28 may be oriented at 90° with respect to a reference axis of the catheter 10. Here, a reference axis is an imaginary line extending from the distal end to the proximal end of the catheter 10, the reference axis following the curvature of the catheter 10. The accessory lumen 30 may comprise a deflection ramp 32 (see, for example, FIGS. 20, 25A and 25B) to urge the emergence of an accessory through the accessory orifice 28 such that the accessory is less likely to be caught in the channel. The deflection ramp 32 is angled with respect to the accessory lumen 30. The emergence angle will facilitate the positioning of one or more accessories into the upper lobe branch vessels of a lung. Inclusion of the accessory channel 30 yields several advantages over single-lumen, single-balloon devices for occlusion of the pulmonary artery for several reasons. For example, catheters according to embodiments of the present invention allow orientation of the drainage channel (primary lumen) of the catheter to provide flow into both the lower lobe (anatomically more predictable) and upper lobe arteries (often occluded by the main balloon in current devices). Further, stability of the catheter is improved by virtue of two point fixation (distal tip and accessory) across the crotch of the pulmonary artery division.

A catheter 10 according to embodiments of the present invention may further comprise an extracorporeal hub at the control end 14 that allows access to the two main suffusion channels (accessory lumen and primary lumen) as well as pilot tubes for the balloon inflation channels (major balloon lumen and minor balloon lumen). See, for example, FIGS. 3, 11A, 11B, and 12, which show access ports for the primary lumen/distal orifice (indicated as 'A'), primary lumen/accessory orifice ('B'), major balloon ('C') and minor balloon ('D'). Also depicted in FIG. 3, the primary lumen may communicate with additional orifices at the distal end of the catheter for improving drainage and/or improving reliability in case the most distal tip orifice becomes obstructed.

The catheter may be produced in accordance with any of a variety of known techniques for manufacturing balloon-type catheter bodies, such as by extrusion of appropriate biocompatible plastic materials. In one embodiment, the catheter may be configured for use in a pulmonary artery of an individual. For example, the length of the catheter and space between components may be selected such that the components can be easily positioned in the pulmonary artery. In one embodiment, the catheter at its thickest has a size of 8-11 F. The catheter may narrow to a 6-8 F dimension containing a major lumen and a minor lumen for a second balloon.

In one embodiment, the invention can be described as a catheter comprising a control end, a working end, a minor lumen, and a first and second major lumen. The minor lumen extends from the control end to the first balloon at the working end of the catheter. The minor lumen is in communication with the first balloon such that the first balloon can be selectively inflated by way of the minor lumen. The minor lumen may have a size of 1-2 F. For example, the minor lumen and the first balloon may comprise a single fluid-tight chamber. By adding fluid to the first balloon by way of the minor lumen, the pressure inside the first balloon increases. The term fluid is used herein to describe both liquids and gases. For example, saline or air may be used to selectively inflate a balloon. The first balloon may be formed such that it can expand (i.e., be inflated) when pressure is applied to the interior of the balloon.

In one embodiment, the working end of the catheter comprises a second balloon in fluid communication with a second minor lumen. The second minor lumen may be identical in size to the first minor lumen. The second balloon is configured to be selectively inflated. For example, the second minor lumen may be separate from the first minor lumen such that either the first minor lumen or the second minor lumen may be inflated or partially inflated. The second balloon is distally located with respect to the first balloon.

The balloon or balloons may also be formed for a particular milieu. For example, the balloon or balloons may be constructed in various sizes, shapes, or hardness. For example, the first balloon may have an inflated diameter of 20-30 mm. Such a diameter may be sufficient to occlude a main pulmonary artery. The length of the catheter may be selected for a particular use as well. For example, a catheter for use in a pulmonary artery may have a first major lumen that extends from the control end to a location at the working end which is 25-100 mm distal with respect to the first balloon. In another example, the first major lumen may extend to a location between the first balloon and the second balloon, if present. The second balloon may have an inflated diameter of 5-15 mm and may be located 25-50 mm distal to the first balloon.

In one embodiment, the first major lumen may be configured to accept another catheter. In this way, the first major lumen acts as a sheath for the second catheter. In one embodiment, the first major lumen may be configured to accept a flow-directed pulmonary artery catheter. In another embodiment, the first major lumen may be configured to receive an anchoring wire. The texture or size of the first major lumen may be selected in order to accommodate either a second catheter, an anchoring wire, or any other component or accessory.

The second major lumen extends from the control end to a location at the working end which is distal with respect to the first balloon. The first major lumen and/or second major lumen have a size of 4-8 F. In embodiments with a second balloon, the second major lumen may extend to a location distal to the second balloon. In embodiments where the first major lumen may be configured to receive an anchoring wire, the second major lumen may terminate at a port configured to allow infusion or drainage. The port may be located proximal with respect to the first balloon or distal with respect to the second balloon.

Figure 2C:
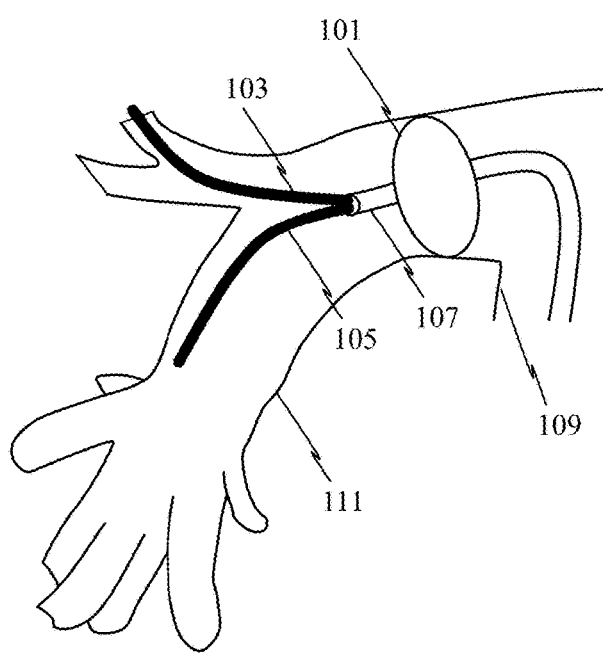
FIG. 2C depicts a catheter having two guide wires in place.
Figure 2B:
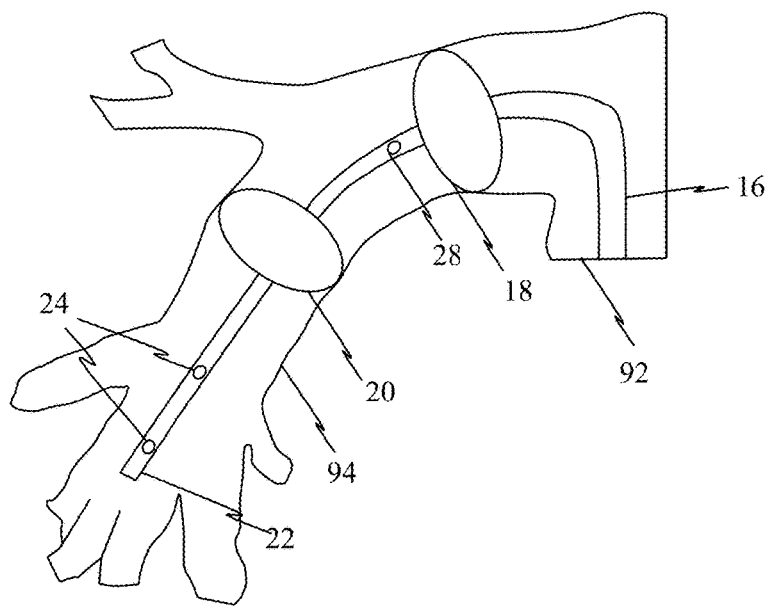
FIG. 2B depicts the catheter of FIG. 2A with balloons inflated.
Figure 2D:
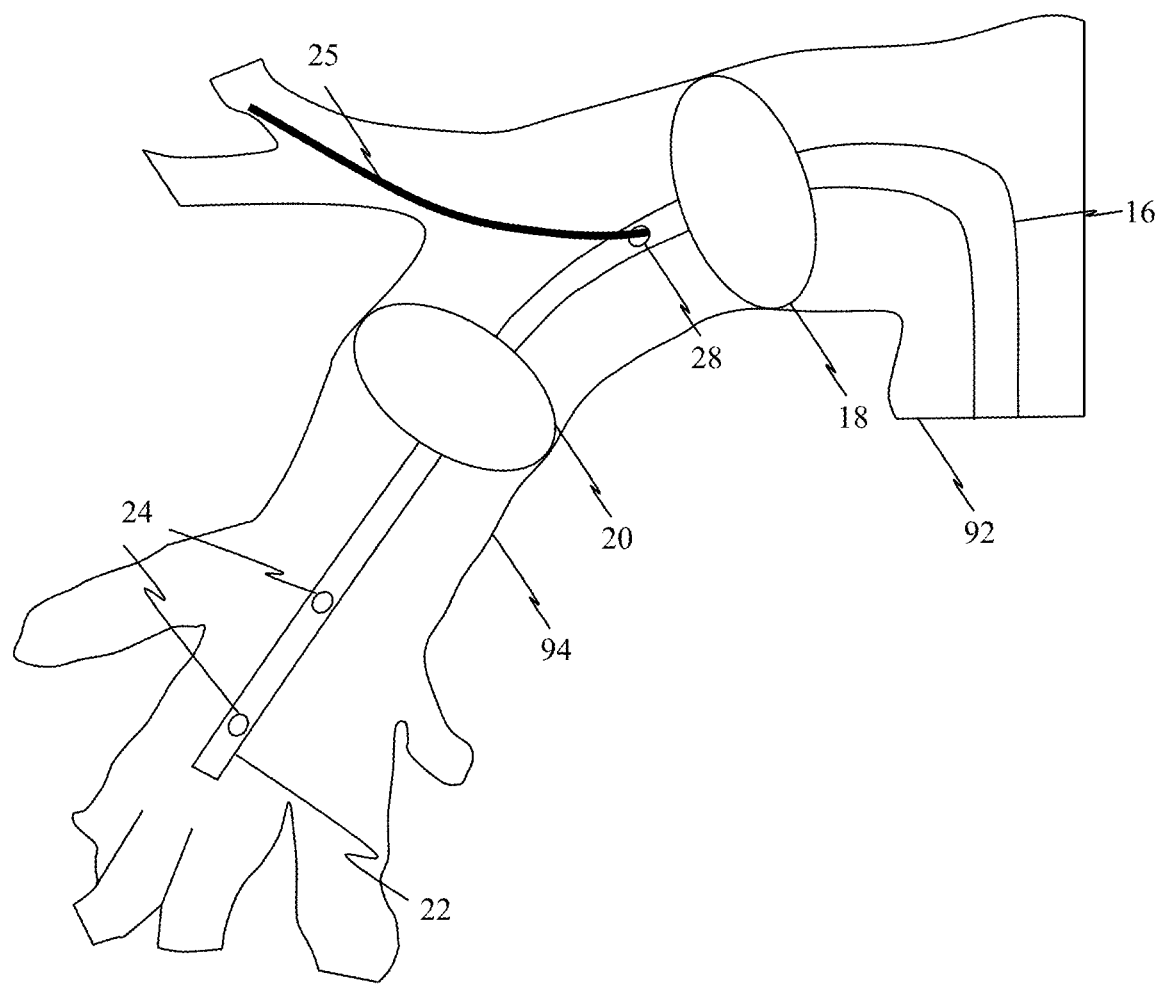
FIG. 2D depicts the catheter of FIGS. 2A and 2B with a guide wire in place.

In one embodiment shown in FIG. 2C, the first major lumen and second major lumen are each configured to receive an anchoring wire. The anchoring wires may be placed in branched arteries (e.g., in a forked fashion) in order to keep the catheter in a substantially constant location.

Figure 20:
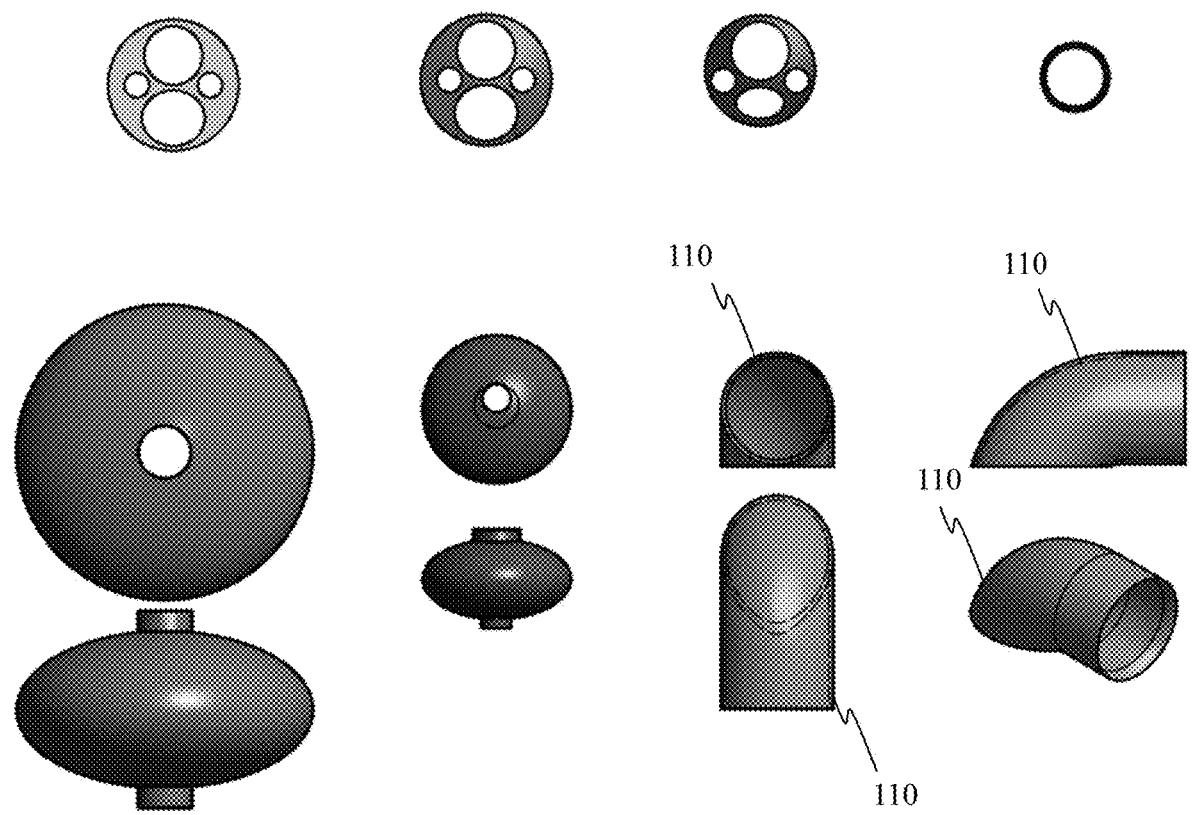
FIG. 20 is an exploded rendering of multiple views of a catheter according to another embodiment of the present invention.
Figure 21A:
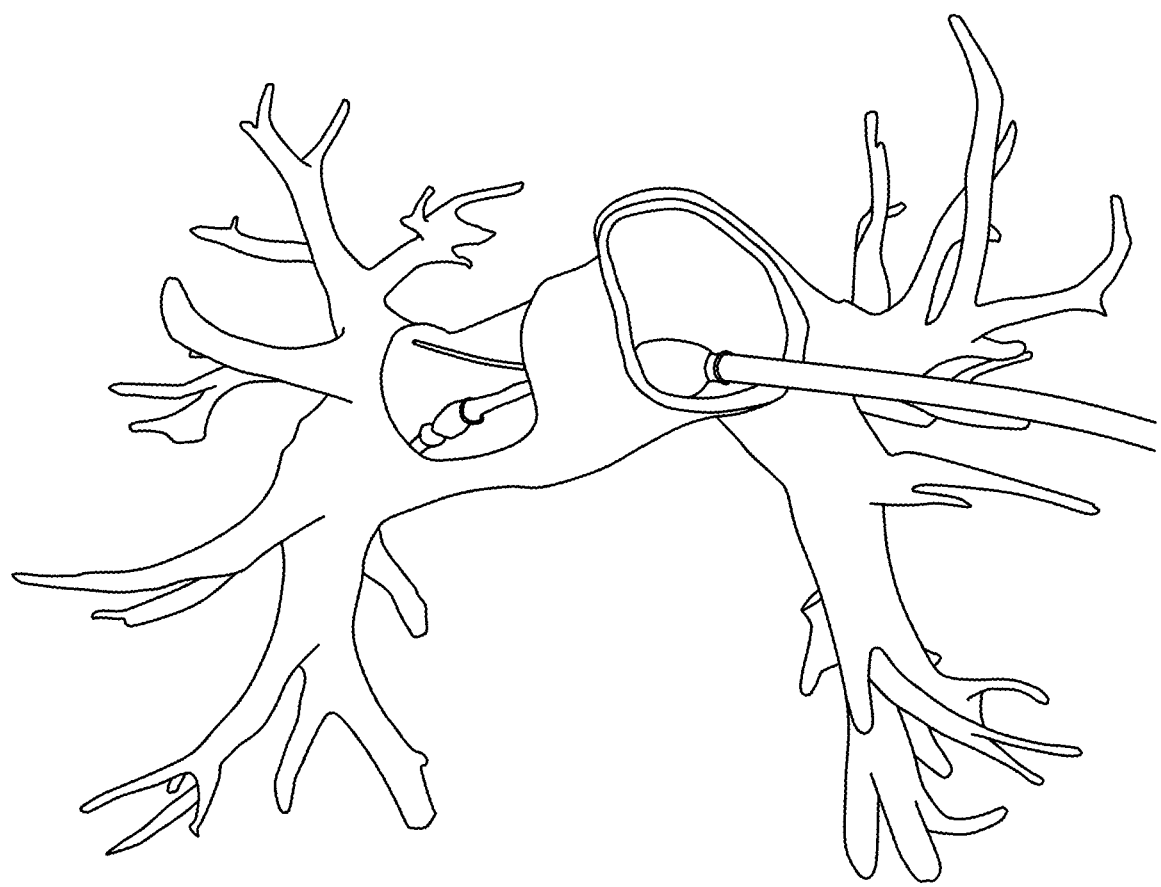
FIGS. 21A and 21B are perspective views of a catheter positioned in situ in a cutaway model of a pulmonary artery.
Figure 21B:
Figure 22A:
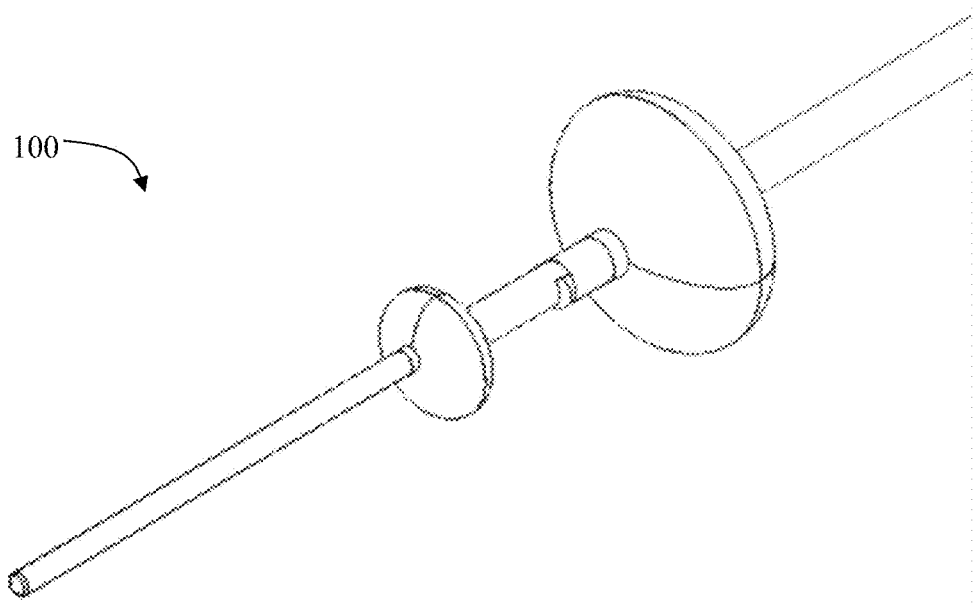
FIG. 22A is a perspective view of a catheter according to another embodiment of the present invention.
Figure 22B:
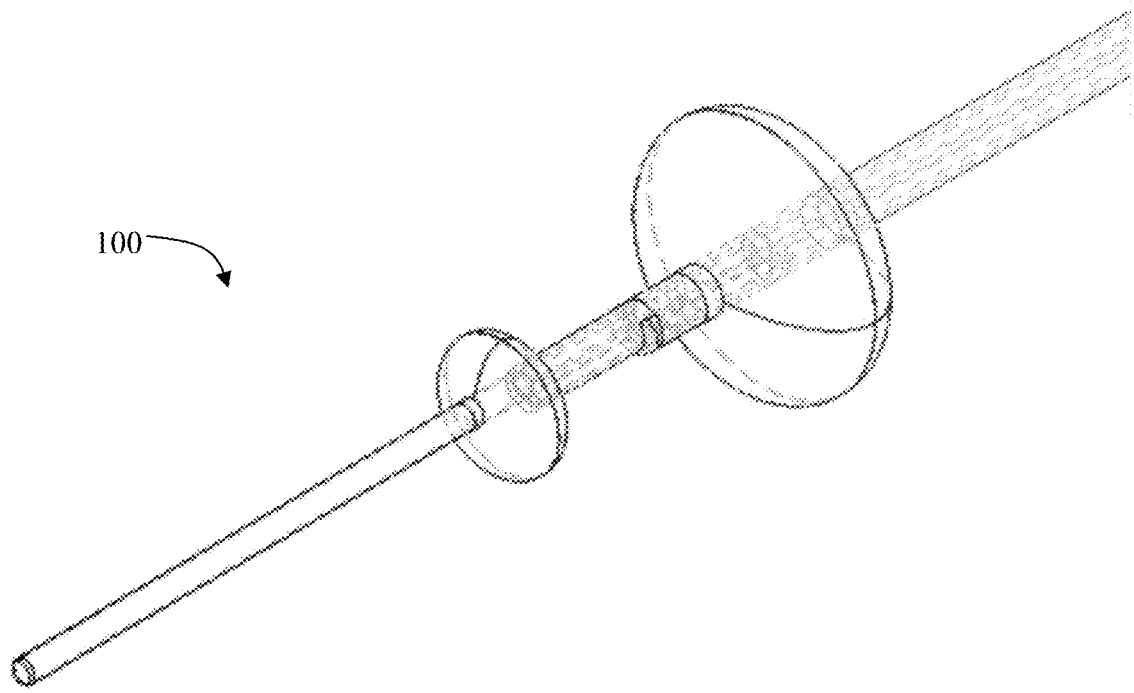
FIG. 22B is a perspective view of the catheter of FIG. 22A showing interior lines.
Figure 23A:
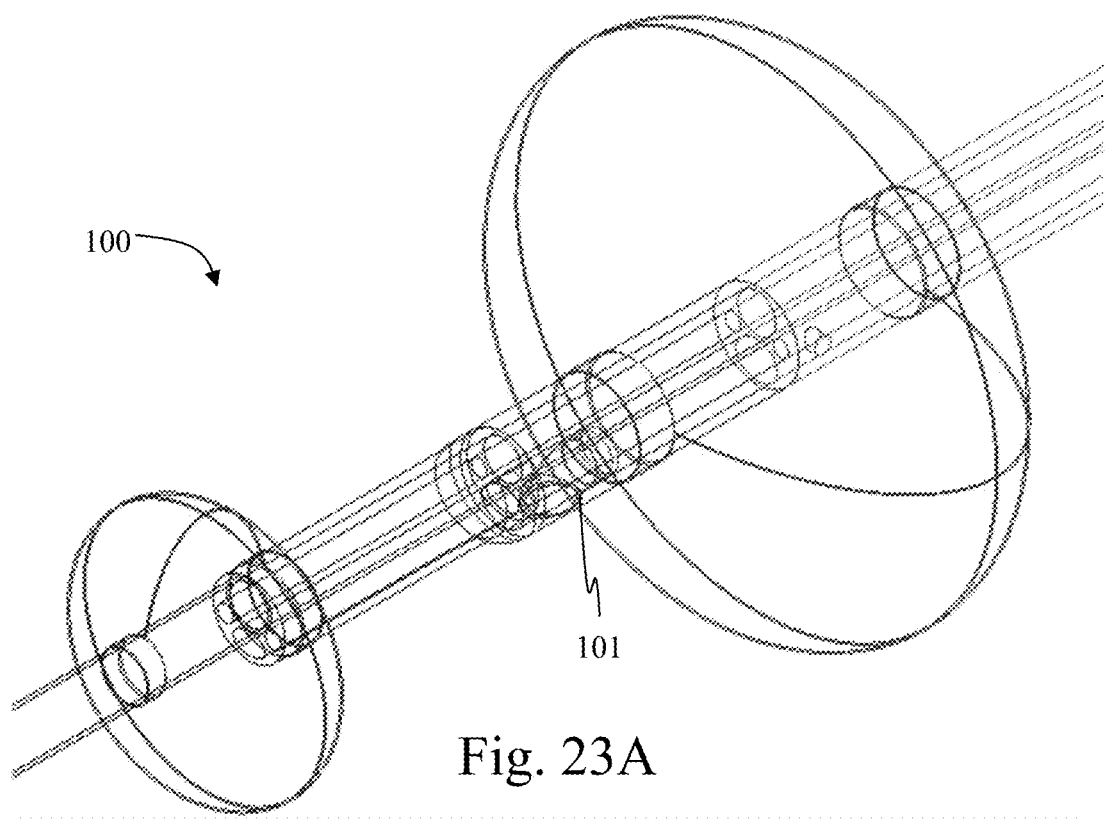
FIG. 23A is a magnified perspective view of the first and second balloons of the catheter of FIG. 22A.
Figure 23B:
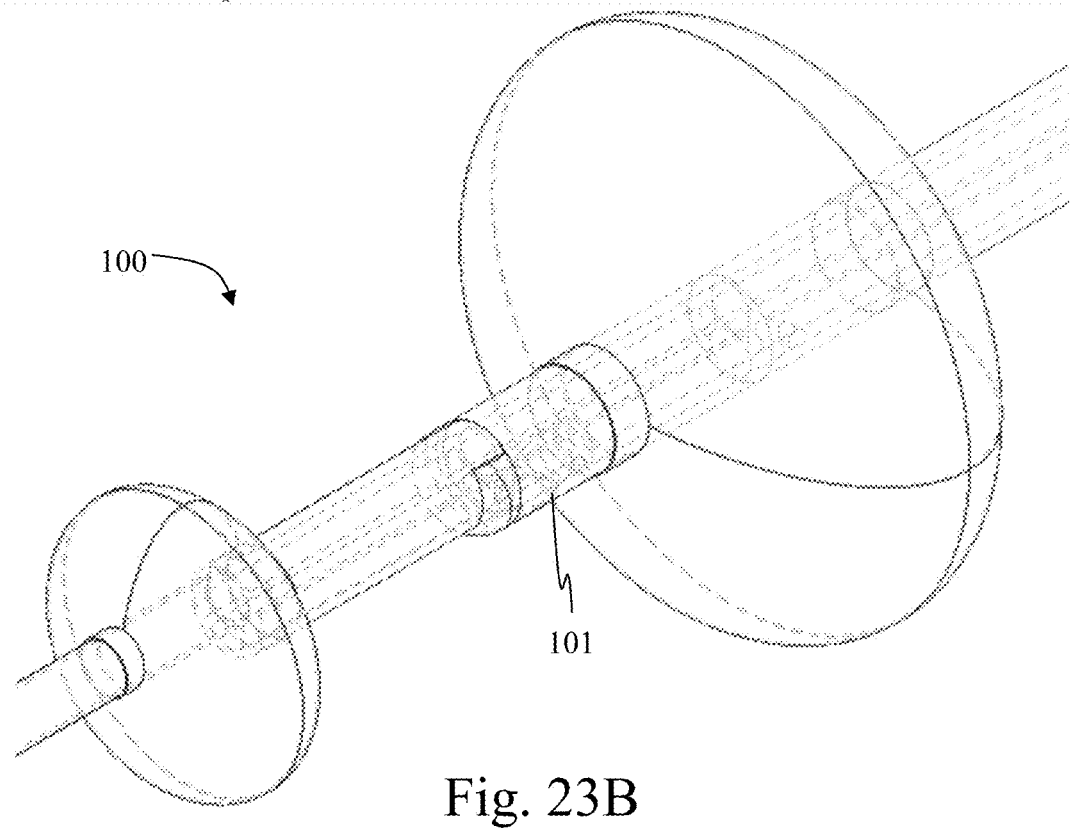
FIG. 23B is a magnified perspective view of the first and second balloons of the catheter of FIG. 22A showing interior lines.
Figure 24A:
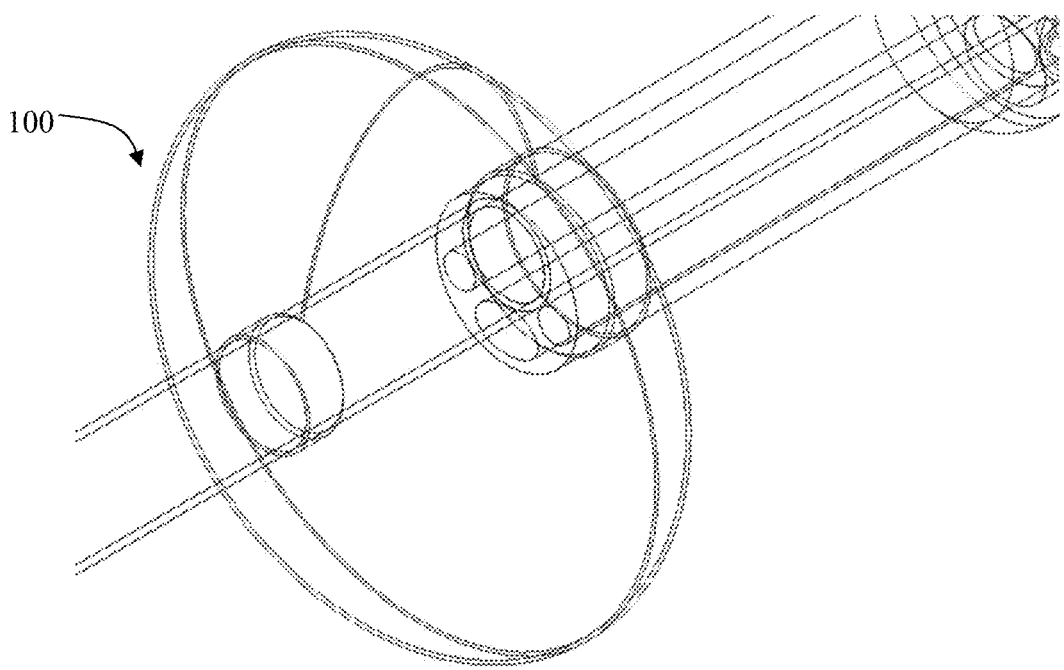
FIG. 24A is magnified perspective view of the second balloon of the catheter of FIG. 22A.
Figure 24B:
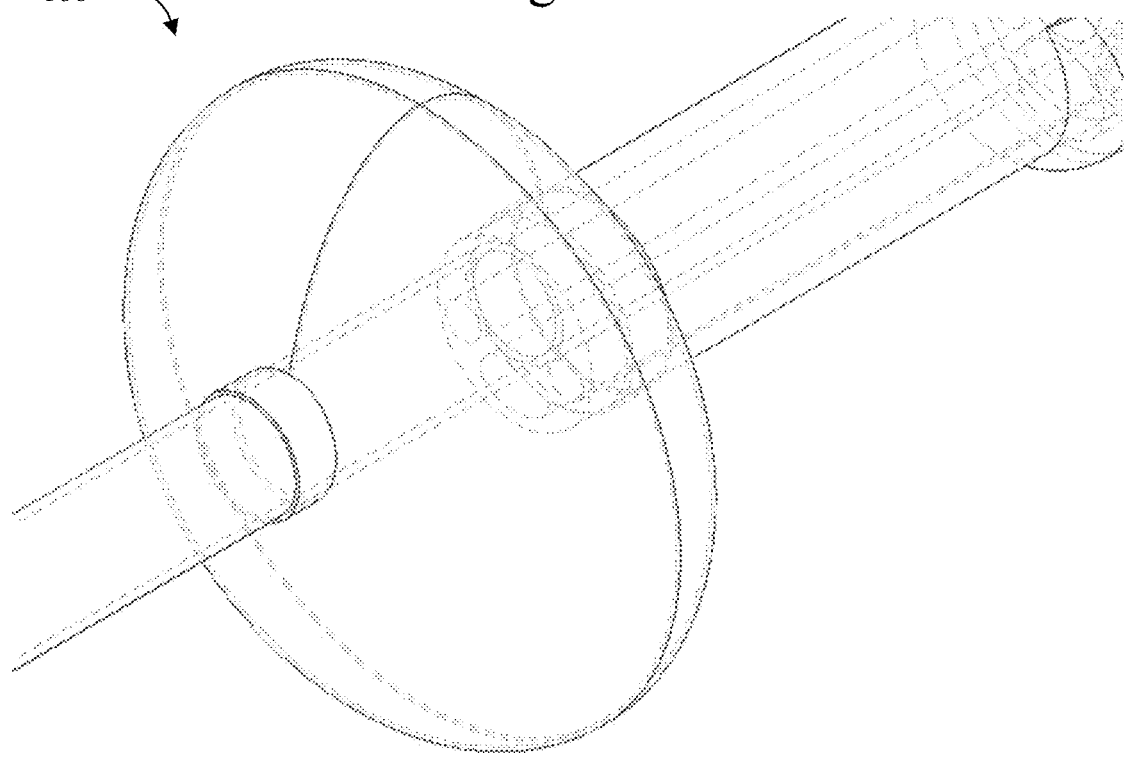
FIG. 24B is a magnified perspective view of the second balloon of the catheter of FIG. 22A showing interior lines.

In another embodiment shown in FIGS. 22A-25B, the catheter 100 further comprises a deflector 101. The deflector 101 may be positioned at the distal end of the first major lumen. The deflector 101 may be configured to deflect an anchoring wire. The anchoring wire is inserted into the first major lumen through the deflector 101. After being deflected, the anchoring wire travels into a branch vessel of a main vessel such that the catheter remains substantially stationary. The deflector 101 may be a ramp, a bead, or other component or combinations of components. Multiple perspectives of an exemplary ramp deflector 110 are shown in FIG. 20.

In another embodiment, the catheter further comprises a venting hole. The venting hole is in fluid communication with the first major lumen. The venting hole may be distally located with respect to the first balloon. The venting holes may be sized or shaped in such a way to improve drainage. These venting holes in the catheter can be used to drain blood from the lung (beyond the balloon occlusion) and infuse the desired chemical agent to act upon the lung tissue.

In one embodiment of the device, the major lumen is enlarged to permit a common 7F, balloon equipped flow-directed pulmonary artery ("PA") catheter to be used. This embodiment allows a user to utilize a familiar or preferred catheter when gaining access to the main pulmonary artery. The catheter of the present invention may be telescoped over the PA catheter in a Seldinger fashion until it is in position to deploy a stabilization wire/catheter through the second major lumen (which does not contain the PA catheter). By inflating the balloon of the PA catheter, this embodiment would allow selective infusion or drainage of the upper and lower branches—one by the flow-directed catheter and the other by the stabilization lumen.

Figure 26:
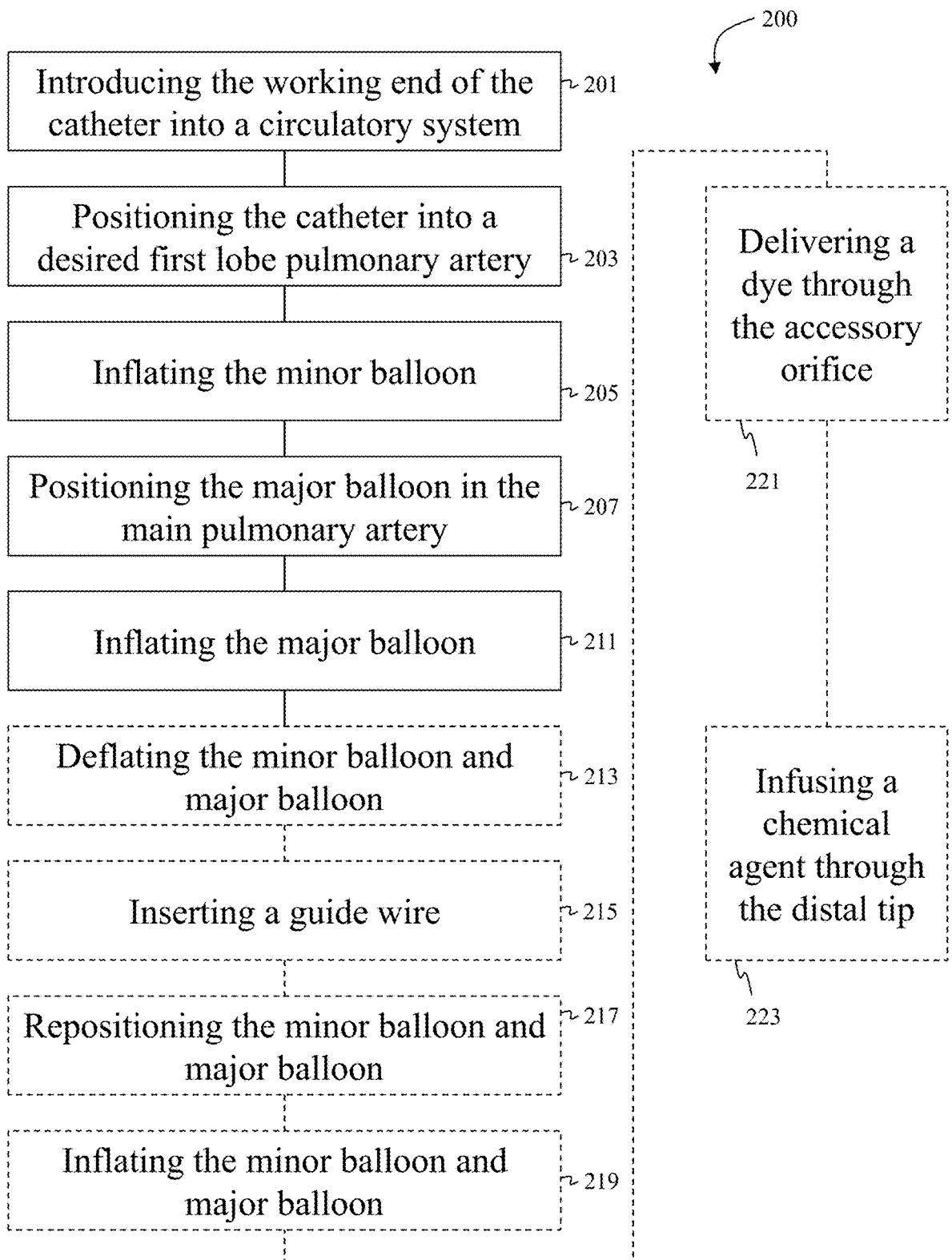
FIG. 26 is a flowchart showing a method according to another embodiment of the present invention.

The present invention may be embodied as a method 200 for selective control of an organ, for example, selective control of pulmonary circulation. FIG. 26 shows such a method. The method 200 may be used with other suitable organs. Under fluoroscopic guidance (or other appropriate guidance), a device similar to any of the above-described catheter (see generally, FIG. 1) is introduced 201 through any large vein, such as, the femoral vein. The device is advanced into the main pulmonary artery through the right heart. After positioning 203 the catheter into the desired lower lobe pulmonary artery, the minor balloon is inflated 205 until there is a reduction in pulsatile distal (primary) lumen arterial waveform (wedge pressure). Then the same process is repeated (i.e., inflated 211) with the major balloon (positioned 207 in the main pulmonary artery) balloon using the accessory lumen to determine the required pressure of the major balloon.

If there is insufficient stability of the device or flow (which, if desired, can be verified by contrast injection) into the upper lobe artery, the method may comprise the step of deflating 213 all, or some, balloons and inserting 215 a guide wire or 5 F catheter through the accessory lumen and orifice and positioned into an upper lobe artery. Then the device can be impacted into a straddling position by repositioning 217 the minor balloon and major balloon and inflating 219 the minor balloon and major balloon. The straddling position offers better stability and the balloon occlusion process and flow assessment process may be repeated until sufficient selective vascular drainage and control is achieved.

A method of the present invention may further comprise the step of confirming placement and proper obstruction of the arteries through the delivery 221 of radiographic dye. The radioactive dye may be delivered 221 using a more proximal port in the device or a secondary catheter to confirm that flow is obstructed. After the dye is delivered 221, transesophageal echocardiographic techniques may be used to confirm the position of the catheter. CT imaging may be used alone or in combination with the transesophageal echocardiographic techniques. The radiographic dye may be delivered 221 multiple times during the method 200.

In general, methods according to embodiments of the invention for use with the lung comprise the steps of placing the catheter through a vein in the neck or the thigh and advancing it centrally through the right side of the heart until a tip of the catheter resides in the artery to the lungs (pulmonary artery). This follows the conventional technique of right heart catheterization. Next, depending on the patient's anatomy, the flow of blood can be interrupted by inflation of one or both balloons on the catheter. If necessary or desirable, an additional small catheter can be placed through one of the channels and advanced into another main branch of the pulmonary artery tree to stabilize the system. Once the native flow of blood is interrupted, separate openings in the catheter can be used to drain blood from the lung (beyond the balloon occlusion) and then infuse 223 the desired chemical agent to act upon the lung tissue.

In one embodiment, the desired chemical agent administered to the individual using this general protocol (which can be adapted by the skilled artisan for treatment of other organs, given the benefit of the present disclosure) is selected to be suitable for treatment of a disease, including but not limited to cancers.

Figure 27:
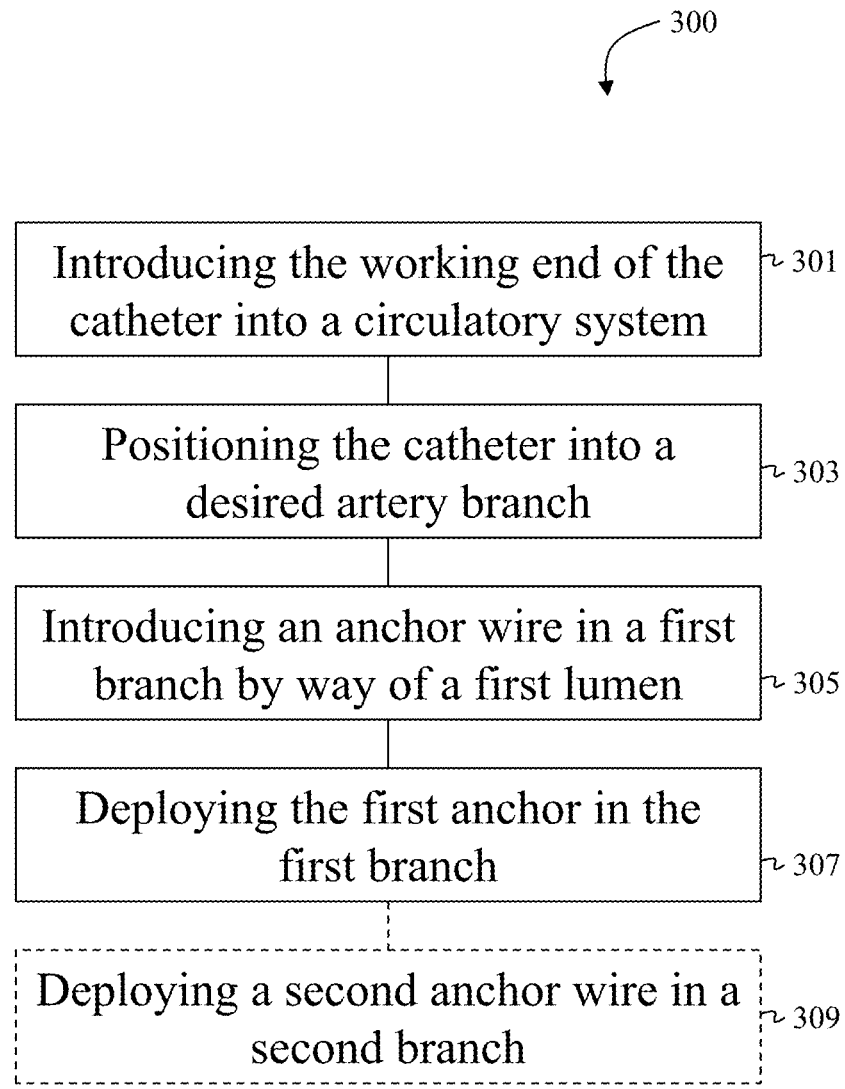
FIG. 27 is a flowchart showing a method according to another embodiment of the present invention.

The invention may also be described as a method 300 for anchoring a catheter in an individual. FIG. 27 shows one such method. In method 300, the catheter may have a working end and a first lumen. The method 300 comprises the steps of introducing 301 the working end of the catheter into a circulatory system of the individual, positioning 303 the catheter into a desired artery having a first branch and a second branch, introducing 305 an anchor wire into the first branch by way of the first lumen, and deploying 307 the first anchor in the first branch using the corresponding lumen to anchor (i.e., stabilize) the catheter in the individual. In one embodiment, the method may further comprise the step of deploying 309 a second anchor wire in the second branch by way of a second lumen.

In one embodiment, the sizes for a non-constrained internal lumen catheter can be calculated. In such a calculation $A_{lt}$=Area of all Lumens, $D_o$=Overall Diameter, $\omega$=Wall thickness needed between lumens and exterior wall, and $D_T$=Total of all Lumen Diameters. Assuming perfect use of internal geometry not constrained by a specific cylindrical shape:

Final overall Area of Cross section=$A_{lt}$+Area of the Exterior (nonshared)Wall Material+Area of the internal (Shared)Wall Material Using $$\frac{\pi D^2}{4}$$

and summing all me lumen area for $A_{lt}$, and using linear integration for the circumferences (shared walls using half of the thickness):

Area of the Exterior (nonshared)Wall Material=$\omega \pi D_o$

Area of the internal (shared)Wall Material=$\omega \pi (D_T - D_o)/2$

Thus, $$\frac{\pi D_o^2}{4} = A_{lt} + \omega \pi D_o + \omega \pi (D_T - D_o)/2$$

Combining terms for use of the quadratic equation to solve for $D_o$:

$$0.25\pi D_o^2 - 0.5\omega\pi D_o - \left(A_{lt} + \frac{\omega\pi D_T}{2}\right) = 0$$

It is considered that embodiments of the invention is suitable for administration of any anti-cancer agent. For example, the invention can be used to administer any one or any combination of the non-limiting examples presented in Table 1. In addition or as an alternative to those agents listed in Table 1, any other therapeutic agent can be used, such as recombinant gene therapy approaches. Any of the agents disclosed herein can be if desired can be delivered in association with conventional drug delivery formulations, such as microspheres. Agents that have potentially adverse effects at or distally from the location where the specific therapy is delivered can be used in combination with delivery of, for instance, a systemic scavenger agent. Any of the agents can be used for targeted delivery, such as for targeting lymphatic tissues that drain the suffused lung, which is an area that is both prone to metastases and has been difficult to target. Any combination of anti-cancer agents can be delivered. Further, the agents can be combined with any carrier, excipient, solvent, etc. to enhance their delivery using the catheter and systems provided by the invention.

It is also considered that the invention will be suitable for therapy of any cancer. In one embodiment, the cancer comprises a solid tumor. In another embodiment, the cancer comprises a blood cancer. Since the lung acts to filter circulating tumor cells from most malignancies, it is a robust location for select anti-cancer immune based therapies. Sarcomas, for example, may only spread to the lung where they resist typical systemic chemotherapy. In particular embodiments, the cancer is selected from the group of cancers consisting of lung cancer, including but not necessarily limited to small cell lung carcinoma and non-small cell lung carcinoma, bladder carcinoma, breast cancer, ovarian cancer, kidney cancer, liver cancer, head and neck cancer, and pancreatic cancer.

In other embodiments, the catheter and systems of the invention can be used to administer one or more agents intended to enhance an immune response to an antigen. The enhanced immune response can comprise humoral and/or cell-mediated responses. The agent can be any antigen to which an enhanced immune response is desired, including but not necessarily limited to proteins, polypeptides and/or peptides which comprise immunogenic epitopes. In certain embodiments, the antigen is one that is expressed primarily or exclusively by cancer cells. In other embodiments, the antigen is one that is expressed primarily or exclusively by an infectious agent, including but not necessarily limited to a bacterium, a virus, a parasitic protozoan, worm, or fungus. Further, the invention can be used to administer an adjuvant to vaccine therapy.

Those skilled in the art will recognize that the dosage of the particular agent being administered to the individual can be adjusted, given the benefit of the present disclosure, based on known factors, such as the gender, age, size and overall health of the individual, as well as the particular disorder being treated, such as the type and stage of cancer or other condition with which the individual has been diagnosed or is suspected of having, or for which the individual is at risk of developing. The invention also permits dosing adjustments which take into account regional delivery of an agent, such as a chemotherapeutic agent. Thus, the invention facilitates using a lower dosage for regional delivery than would otherwise be required using conventional systemic delivery methods.

The disclosed catheters can be used during performance of intravascular techniques for localized delivery of therapeutic and/or prophylactic can be used with known techniques, which include but are not necessarily limited to, the following: arterial chemoembolization, bronchial artery infusion (BAI), isolated lung perfusion (ILP), and in preferred embodiments, for organ suffusion, including but not necessarily limited to, lung suffusion. Based on previous studies of bronchial artery infusion, only about 10 percent of lung tumors derive the preponderance (over 75%) of their blood supply from systemic arteries rather than pulmonary artery branches. Accordingly, this catheter will be useful for the majority of patients. A schematic diagram of the major techniques is provided in FIG. 24. Table I lists some clinical studies involving the techniques. Contraindications of the procedures are generic, such as pregnancy and breast-feeding, and allergy to iodinated contrast media. Typical side effects include fever, chest pain, cough, hemoptysis, vomiting, mild and transient hemodynamic changes, and hematoma at the site of percutaneous puncture. Regional chemotherapy using these techniques can be followed up with systemic chemotherapy, radiotherapy, and/or surgical resection.

TABLE I

Clinical studies of regional chemotherapy for primary and metastatic cancer

| Reference | Drug ± Adjuvant therapy | Study population[a] | Response[a] | Complications[a] |
|---|---|---|---|---|
| Pulmonary artery chemoembolization | | | | |
| Vogl, et al., 2008 (28) | Lipiodol, mitomycin C and Spherex ™ microspheres | 52 cases with 106 lung metastases | 31% response, 21% stable disease | |
| Bronchial artery infusion | | | | |
| Neyazaki, et al., 1969 (41) | Mitomycin C | 27 cases | tumor volume reduced in 52% | Chemical pneumonitis (1), chest wall skin erythema (1) |
| Watanabe, et al., 1990 (42) | Carboquone, mitomycin C, and/or nimustine | 106 cases of stage III hilar tumor | tumor volume reduced in 41% and 84% with single and | Transient hemiplagia (1) |

TABLE I-continued

Clinical studies of regional chemotherapy for primary and metastatic cancer

| Reference | Drug ± Adjuvant therapy | Study population[a] | Response[a] | Complications[a] |
|---|---|---|---|---|
| Shi, et al., 1995 (44) | Carboplatin and etopside, with pulmonary artery infusion | 10 cases | triple drug therapy, respectively 80% response | |
| Wang, et al., 1996 (43) | Adriamycin, cisplatin, etopside, and/or mitomycin C, with radiotherapy | 63 cases of locally advanced bronchogenic cancer | 44% complete response, 40% partial response | Hematoma at site of percutaneous puncture (1) |
| Osaki, et al., 1999 (33) | Camptothecin 11 and cisplatin, with surgical resection in some cases | 7 cases of central early stage squamous carcinoma | 86% complete response | Bronchial ulcer (3), pulmonary hemorrhage and death after 3 months (1) |
| Koshiishi, et al., 2000 (39) | Camptothecin 11, cisplatin, and/or etopside | 17 cases of advanced cancer | 12% partial response | Severe chest symptoms (13) |
| Liu, et al., 2001 (35) | Cisplatin, doxorubicin, and/or mitomycin C | 76 cases of moderate or advanced NSCLC | 51% and 24% 2-year survival rate with and without Chinese herbal medication, respectively | |
| So, et al., 2004 (34) | Cisplatin, and carinal resection | 3 cases of locally advanced NSCLC | 100% complete response | |
| Nakanishi, et al., 2008 (47) | Multi-arterial infusion with cisplatin, doxorubicin, and/or gemcitabine | 32 cases | 3% complete response, 50% partial response | Interstitial pneumonia (7) hepatic failure (2), respiratory failure with $PaO_2$ <60 (12) |
| Isolated Lung Perfusion | | | | |
| Johnston, et al., 1995 (60) | Or total lung perfusion with doxorubicin or cisplatin | 8 cases of metastatic sarcoma or diffuse bronchioloalveolar carcinoma | 0% response | Pneumonia (1), respiratory failure (1) |
| Pass, et al., 1995 (61) | TNF-α and interferon-γ | 20 cases of pulmonary metastases | 15% partial response | Lung abscess (1), TNF-α leakage and systemic toxicity (1) |
| Ratto, et al., 1996 (62) | Cisplatin | 6 cases of metastatic sarcoma | | Interstitial and alveolar edema (2) |
| Burt, et al., 2000 (58) | Doxorubicin | 8 cases of metastatic sarcoma | 0% response | Pulmonary fibrosis (1), reduced pulmonary function (7) |
| Schroder, et al., 2002 (63) | Cisplatin following metastectomy | 4 cases of metastatic sarcoma | 75% disease-free after 1 year | Localized pulmonary edema (4), reduced pulmonary function at 3 weeks (3) |
| Hendriks, et al., 2004 (59) | Melphalan followed by metastectomy | 16 cases of resectable pulmonary metastases | | Chemical pneumonitis (2), localized pulmonary edema (3), pneumonia (1), pneumothorax (1) |
| Thoracoscopic lung suffusion | | | | |
| Demmy, et al., 2009 (69) | Cisplatin with systemic chemotherapy | 4 cases of stage IV NSCLC | 14%-96% reduction in tumor volume | |

[a]Descriptions of cases, responses, and complications are from publications describing the studies
[b]Number of cases are shown in parentheses Arterial Chemoembolization Transcatheter arterial chemoembolization has been used successfully for the treatment of primary and secondary hepatic malignancies, and is currently under evaluation as a less invasive option for the treatment of lung cancer. Also referred to as transpulmonary chemoembolization, it does not require thoracotomy, can be performed multiple times, and can be done percutaneously through an endovascular catheter with fluoroscopic guidance. Typically, a 5-French catheter in a 7-French sheath is placed transfemorally into the pulmonary artery and advanced fluoroscopically over a guidewire into the segmental artery of interest. There a 7 mm balloon catheter is placed. The aim of the procedure is to selectively obstruct arterial supply to induce ischemic necrosis in the tumor with minimal damage to the normal lung parenchyma, while simultaneously administering a chemotherapeutic agent. The embolization prevents washout of the agent and allows for its administration at a high dosage. Embolizates such as polyvinyl alcohol and steel coils are used for permanent occlusions whereas embolization by agents like lipiodol, degradable starch microspheres and gelatin sponges is temporary. Use of drug-eluting beads for controlled release of the therapeutic agent over longer periods of time is also being investigated.

Temporary chemoembolization of the lung with carboplatin and microspheres was first demonstrated in 2002 in a rat model of solitary adenocarcinoma. Injection of microspheres into the pulmonary artery interrupted perfusion for seven minutes and retarded capillary blood flow for 14 minutes. The procedure was found to be more effective than systemic chemotherapy and as effective as isolated lung perfusion. In humans, chemoembolization of segmental pulmonary arteries using mitomycin, lipiodol, and microspheres for the treatment of lung metastases has been performed in 52 patients, all of whom tolerated it well without major complications or side effects. Tumor volume regression was observed in 16 of them and a stable tumor state was documented in nine. A balloon catheter was used to prevent outflow of reagents into the pulmonary artery and to detect any arteriovenous shunting, an indication to terminate the procedure. Long term histological changes such as fibrosis indicative of toxicity of the procedure have not been observed in a pig model. Potential serious side effects include paraplegia, because of embolization or occlusion of spinal arteries with collateral connections to the pulmonary and bronchial circulation.

Bronchial Artery Infusion

Localized chemotherapy through arterial infusion is especially useful when a tumor in an organ receives its blood supply differently from the rest of the organ as is seen in cases of hepatic metastases in which the tumors are vascularized by the hepatic artery whereas normal hepatocytes are perfused by the portal vein. For instance, there are some cases of lung metastases where the tumors are mainly supplied by the bronchial arteries and this phenomenon is more likely to occur centrally.

Bronchial artery involves the insertion of a transfemoral 5-French catheter into a bronchial artery guided by angiography. Superselective arterial catheterization can be achieved by using coaxial microcatheters. Single or multiple anti-cancer reagents are then introduced. The treatment is repeated after some weeks. It has been used both as a primary treatment and as a palliative measure. The technique has also been used in combination with radiotherapy or isolated lung perfusion. It should be noted that it is possible for the ipsilateral bronchial artery to not be the feeding artery. Multi-arterial infusion chemotherapy has been demonstrated when there are multiple feeding arteries. Precise identification and use of the right feeding artery, and tumor identification by angiography is important for efficacy of the procedure. BAI has also been used to treat non-lung cancers such as thymic neoplasias. Potential serious side-effects of the technique include spinal cord injury, bronchial or esophageal ulceration, and formation of a bronchoesophageal fistula.

Isolated Lung Perfusion ("ILP")

Selective delivery of chemotherapeutic agents by isolated limb perfusion in cases of melanoma and sarcoma, and by hepatic perfusion for unresectable liver tumors and metastases from colorectal cancer has been described. Isolated perfusion for the lung involves the cannulation of both pulmonary artery and vein for connecting them to an extracorporeal flow system that establishes a perfusion circuit. Bilateral ILP can be achieved through staged unilateral ILPs, or through total lung perfusion with cannulation of the ascending aorta and the right atrium for a cardiopulmonary bypass. ILP allows for selective delivery of reagents to the lungs through the pulmonary artery line of the circuit, as well as localized hyperthermia which can cause an increased uptake and cytotoxicity of drugs in the lung tissue. Systemic anticoagulation therapy is needed, and the bronchial arterial blood flow is occluded by snaring of the main bronchus. Lung ventilation is maintained for even distribution of drugs. Perfusion is performed for 30-90 minutes.

The ILP method was first described in 1959 during which complete separation of the systemic and pulmonary circulations was achieved using two extracorporeal systems. Regional chemotherapy for lung cancer using the technique was first demonstrated in dogs by Pierpont and Blade in 1960 and was first reported for humans, with a 50% postoperative mortality rate, in 1986. The safety of the ILP technique and the lack of long-term toxicity, in a dog model, was established in 1983. In experimental studies on animals such as sheep, rats, pigs and dogs, chemotherapeutic agents such as cisplatin, melphalan, doxorubicin, and tumor necrosis factor (TNF)-alpha have been administered using methods ranging from total lung perfusion with cardiopulmonary bypass to isolated single-pass lung perfusion to ex vivo perfusion of resected lungs. The procedure has been found safe in humans in six phase I clinical trials that have involved a total of 62 patients. However, ILP is a cumbersome method that requires thoracotomy for safe cannulation of the pulmonary artery and vein and extracorporeal circuits and thus and risks painful incisions for a group with anticipated brief remaining quality of life. Adverse systemic inflammatory responses by perioperative release of cytokines or direct toxicities through collateral leaks occur frequently. Variations to the method, such as stop-flow occlusion and video-assisted transcatheter cannulation, have been investigated in animals to reduce its complexity and associated morbidity. Ex vivo lung perfusions with camptothecin or a doxorubicin prodrug have been performed to study drug kinetics and to show low cytotoxicity.

Lung Suffusion

The term "suffusion" has been defined as the slow diffuse permeation of the tissues by an injectate during arterial or venous occlusion. Unlike methods for arterial infusion or isolated perfusion, those for suffusion require neither permanent occlusion nor recirculation. The technique involves isolating chemotherapy into the lung by interventional radiologic control of the pulmonary artery and endoscopic control of the pulmonary veins. The suffusion method was first described in a canine model in 2002. A minimally invasive approach and its short-term potential were established using a non-toxic tracer compound. Rapid permeation of the lung and 75% of tracer remaining isolated the lung for 30 minutes was observed.

One phase I clinical trial on four stage IV NSCLC patients has been conducted. Cisplatin was delivered for a dwell-time of 30 minutes before the lung was reperfused. While described in greater detail in the cited report, briefly, the suffusion was achieved by the steps listed in Table II.

TABLE II

Sequence of Lung Suffusion

| Step | Technical Details | Special Equipment/Comments |
|---|---|---|
| Vein isolation | Routine single lung ventilation VATS ensnarement through 3 ports Ports wounds closed temporarily Lateral positioning changed to supine | Extra-long silicone vessel loops Loops sutured without tension to closest port site subcutaneous tissue. |
| Central venous cannulation | Femoral (preferred) or jugular venous. | Large sheath sufficient to introduce PA occluder |
| Pulmonary artery occluder placement | Fluoroscopic guidance | Deflectable tip wire Guidewires of various stiffness Low pressure occlusion balloon (Arndt ™ 9 French$^a$) |
| Vascular isolation and lung drainage | PA balloon inflated. Collapse ipsilateral lung Vein snares applied. PA blood aspirated and reinfused. | Air used in balloon to reduce risk of artery damage. |
| Lung Suffusion | Ipsilateral lung reinflated and ventilated. Chemotherapy administered | PA pressure constantly monitored |
| Lung reperfusion | Vein snares released and extracted. PA balloon collapsed and removed | PA or lung samples obtained as needed before or after reperfusion |

PA—Pulmonary artery;
VATS—Video-assisted thoracoscopic surgery
$^a$Off-label use Leakage into the systemic circulation was minimal as evidenced by an approximate five-fold higher level of the drug in the pulmonary circulation at the end of the dwell-time. Tumor volume was reduced 14% to 96%. While this might have been due partially to systemic chemotherapy that began within 2 weeks of the suffusion, one patient had progression of non-suffused systemic metastases while the suffuse lung had stable disease. Differential pulmonary toxicity was not seen although a reduction in overall diffusing capacity of the lungs, similar in extent to that seen with systemic chemotherapy, was observed. Since that report, a total of ten patients have been treated by suffusion (unpublished data). One of 10 could not tolerate suffusion, which is consistent with the expectation that 10% of patients have a large contribution of their tumor by systemic arteries. Of the remaining patients, 4 of 5 patients with evaluable disease showed control or reduction of the main tumor in the suffused lung while there was growth of tumor in other parts of the body despite getting systemic chemotherapy. The maneuvers used in the method are similar to commonly performed procedures like pulmonary catheterization and pulmonary vein dissection.

It will be recognized from the foregoing description that, in certain embodiments, the catheter provided by the invention can be used for regional lung chemotherapy techniques that comprise suffusion of chemotherapeutic agent(s) to the lungs of an individual with lung cancer.

Any indications of range throughout this disclosure should be interpreted as inclusive of the listed values.

Although the present invention has been described with respect to one or more particular embodiments, it will be understood that other embodiments of the present invention may be made without departing from the spirit and scope of the present invention. Hence, the present invention is deemed limited only by the appended claims and the reasonable interpretation thereof.

What is claimed is:

1. A catheter for use with an anchoring wire in a pulmonary artery, the catheter comprising:
   a control end configured to remain outside of a body of an individual;
   a first lumen, a second lumen, and a third lumen;
   a working end comprising:
     a major balloon in fluid communication with the first lumen and configured to be selectively inflated;
     a minor balloon distally located along the catheter with respect to the major balloon, the minor balloon in fluid communication with the second lumen and configured to be selectively inflated;
     an accessory orifice formed in a sidewall of the catheter and located between the major balloon and the minor balloon, the accessory orifice in communication with the third lumen; and
     a distal tip distally located along the catheter with respect to the minor balloon, the distal tip having an orifice in communication with a port at the control end by way of a primary lumen;
   wherein the third lumen is configured to receive the anchoring wire therethrough;
   wherein the third lumen has a deflection ramp configured to assist the movement of the anchoring wire through the accessory orifice to stabilize the catheter; wherein an angle of the deflection ramp is configured to facilitate the positioning of the anchoring wire into an upper lobe branch vessel of a lung;
   wherein the third lumen has a size of 4-6 F.;
   wherein the catheter has a first diameter proximal to the major balloon and a second diameter distal to the major balloon, and the first diameter is greater than the second diameter; and
   wherein the primary lumen is configured to drain fluid from a location at the distal tip.

2. The catheter of claim 1, wherein the control end is configured for manipulation by an operator.

3. The catheter of claim 1, wherein the first lumen and the second lumen each have a size of 1-2 F.

4. The catheter of claim 1, wherein the major balloon is configured to occlude blood flow in a main pulmonary artery of a patient when inflated and the minor balloon is configured to occlude blood flow in a branch pulmonary artery of a patient when inflated.

5. The catheter of claim 1, wherein the third lumen is configured such that the anchoring wire may be introduced by an operator into the third lumen.

6. The catheter of claim 1, wherein the third lumen has a size of 5 F.

7. The catheter of claim 1, wherein the first lumen is in communication with a port at the control end of the catheter for introduction or removal of a fluid.

8. The catheter of claim 1, wherein the accessory orifice is oriented at 90 degrees with respect to a reference axis of the catheter.

9. The catheter of claim 1, wherein the deflection ramp is configured to assist movement of the anchoring wire through the accessory orifice to orient the primary lumen.

10. The catheter of claim 1, wherein the deflection ramp is an inner wall of the accessory lumen and forms a solid sliding surface configured to contact the anchoring wire.

11. The catheter of claim 10, wherein the deflection ramp has a fixed angle.

12. The catheter of claim 1, wherein a size of the major balloon is greater than a size of the minor balloon.

13. The catheter of claim 1, wherein the major balloon and the minor balloon are each disposed in a fixed position along the catheter.

14. The catheter of claim 1, wherein a length of the third lumen is less than a length of the anchoring wire.

15. The catheter of claim 1, wherein the deflection ramp forms a curved surface configured to contact the anchoring wire.

16. The catheter of claim 15, wherein the curved surface terminates at the accessory orifice.

17. The catheter of claim 1, wherein the accessory orifice is located closer to the major balloon than the minor balloon.

18. A catheter for use with an anchoring wire in a pulmonary artery, the catheter comprising:
- a control end configured to remain outside of a body of an individual;
- a first lumen, a second lumen, and a third lumen;
- a working end comprising:
  - a major balloon in fluid communication with the first lumen and configured to be selectively inflated;
  - a minor balloon distally located along the catheter with respect to the major balloon, the minor balloon in fluid communication with the second lumen and configured to be selectively inflated;
  - an accessory orifice formed in a sidewall of the catheter and located between the major balloon and the minor balloon, the accessory orifice in communication with the third lumen; and
  - a distal tip distally located along the catheter with respect to the minor balloon, the distal tip having an orifice in communication with a port at the control end by way of a primary lumen;

wherein the third lumen is configured to receive the anchoring wire therethrough;

wherein the third lumen has a deflection ramp configured to assist the movement of the anchoring wire through the accessory orifice to stabilize the catheter; wherein an angle of the deflection ramp is configured to facilitate the positioning of the anchoring wire into an upper lobe branch vessel of a lung;

wherein the third lumen has a size of 4-6 F., and;

wherein the primary lumen is configured to drain fluid from a location at the distal tip.

* * * * *